United States Patent
Shibuya et al.

(10) Patent No.: US 6,204,278 B1
(45) Date of Patent: *Mar. 20, 2001

(54) ANILIDE COMPOUNDS, INCLUDING USE THEREOF IN ACAT INHIBITITION

(75) Inventors: Kimiyuki Shibuya, Saitama-ken; Katsumi Kawamine; Yukihiro Sato, both of Tokyo; Toshiyuki Edano; Souhei Tanabe, both of Saitama-ken; Masami Shiratsuchi, Tokyo, all of (JP)

(73) Assignee: Kowa Company, Ltd., Aichiken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/858,244

(22) Filed: May 19, 1997

(30) Foreign Application Priority Data

May 17, 1996 (JP) ................................ 8-158743
Mar. 25, 1997 (JP) ................................ 7-088660

(51) Int. Cl.$^7$ ................... A61K 31/423; C07D 263/58
(52) U.S. Cl. ................ 514/375; 514/367; 514/388; 514/395; 548/161; 548/164; 548/171; 548/221; 548/222
(58) Field of Search ................ 548/221, 222; 514/375

(56) References Cited

U.S. PATENT DOCUMENTS

| | | | |
|---|---|---|---|
| 3,720,686 | 3/1973 | Narayanan et al. | 260/309.2 |
| 4,833,243 | * 5/1989 | Forster et al. | 540/480 |
| 5,290,801 | * 3/1994 | Higley et al. | 514/395 |
| 5,362,878 | 11/1994 | Chang et al. | 546/296 |

FOREIGN PATENT DOCUMENTS

| | | |
|---|---|---|
| 29 03 966 A | 8/1980 | (DE) . |
| 0 372 445 A1 | 6/1990 | (EP) . |
| 0 418 071 A2 | 3/1991 | (EP) . |
| 0 477 778 A2 | 4/1992 | (EP) . |
| 2 058 773 A | 4/1981 | (GB) . |
| 2 093 835 A | 9/1982 | (GB) . |
| 4-139172 | * 5/1992 | (JP) . |
| WO 93/23392 | 11/1993 | (WO) . |

OTHER PUBLICATIONS

J. Sawlewicz et al., *Rozprawy Wydz.*, 9:135–140 (1992).
R. Misra et al., *Journal of Pharmaceutical Sciences*, 65(3);405–408 (1976).
I. Husain et al., *Journal of the Indian Chemical Society*, 57(4):451–453 (1980).
N.A. Aliev, *Chemical Abstracts*, 94(21):715, Abstract No. 174947 (1981).
A.M. Mahmoud et al., *Acta Pharm. Jugosl*, 329(1):45–51 (1982).
A. Mahmoud et al., *Gazzetta Chimica Italiana*, 112(1–2);55–56 (1982).
S. Tripathi et al., *Indian Journal of Chemistry*, 21B(4):379–390 (1982).
A. Hammam et al., *Journal of Chemical and Engineering Data*, 27(2):207–208 (1982).
H. El-Sherief et al., *Journal of the Indian Chemical Society*, 60(1):58–60 (1983).
E. Sidoova et al., *Chemical Abstracts*, 1209(17):1081, Abstract No. 217664a (1994).
E. Sidoova et al., *Chemical Abstracts*, 120(21):1068, Abstract No.270378m (1994).
O. Orio et al., *Chemical Abstracts*, 69(23):9034, Abstract No. 96541a (1968).
Derwent Abstract, abstracting JP 04 139 172 A May 1992.
R. Wilde et al., *Bioorganic & Med. Chem. Lett.*, 5(2):167–172 (1995).
T. Satoh et al., *Chem. Pharm. Bull.*, 33(2):647–654 (1985).
Derwent Abstract, abstracting J57122062, 1982.

* cited by examiner

Primary Examiner—Laura L. Stockton
(74) Attorney, Agent, or Firm—Peter F. Corless; Christine C. O'Day; Edwards & Angell, LLP

(57) ABSTRACT

The invention provides novel anilide compounds and pharmaceutical compositions comprising them.

The invention relates to compounds of a formula:

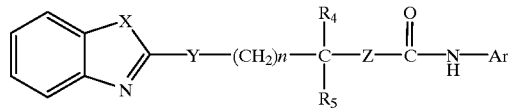

where
Ar is an optionally-substituted aryl group;
$R_4$ and $R_5$ are the same or different, and each is a hydrogen atom, a lower alkyl group, or a lower alkoxy group; and $R_4$ and $R_5$ may together form a lower alkylene group of which one or more methylene moieties may optionally be substituted by oxygen and/or sulfur atoms;
X is —NH—, or oxygen or sulfur atom;
Y is —NH—, an oxygen or sulfur atom, or a sulfoxide or sulfone group;
Z is a single bond, or —NH$_6$—;
$R_6$ represents a hydrogen atom or a lower alkylene group; and
n is an integer of from 0 to 15;
and their salts and solvates.

The compounds of the invention are useful as pharmaceutical compositions, especially as acyl coenzyme A cholesterol acyltransferase (ACAT) inhibitors.

19 Claims, No Drawings

ANILIDE COMPOUNDS, INCLUDING USE THEREOF IN ACAT INHIBITITION

TECHNICAL FIELD OF THE INVENTION

The present invention relates to novel anilide compounds and pharmaceutical compositions comprising them. More precisely, the present invention relates to compounds of a general formula (I):

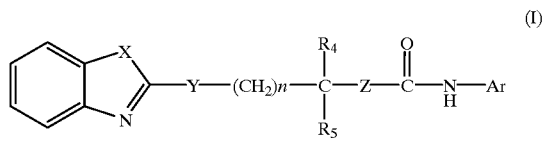

wherein
- Ar is an optionally-substituted aryl group;
- $R_4$ and $R_5$ are the same or different, and each represents a hydrogen atom, a lower alkyl group, or a lower alkoxy group; and $R_4$ and $R_5$ may together form a lower alkylene group of which one or more methylene moieties may optionally be substituted by oxygen and/or sulfur atoms;
- X is —NH—, or an oxygen or sulfur atom;
- Y is —NH—, an oxygen or sulfur atom, or a sulfoxide or sulfone group;
- Z is a single bond, or —NH$_6$—;
- $R_6$ represents a hydrogen atom or a lower alkylene group; and
- n is an integer of from 0 to 15;
- provided that, when X and Y are sulfur atoms, $R_4$ and $R_5$ are hydrogen atoms, Z is a single bond and n is 0, then Ar must not be a phenyl or p-chlorophenyl group,
- when X and Y are sulfur atoms, $R_4$ and $R_5$ are hydrogen atoms, Z is a single bond and n is 1, then Ar must not be a phenyl group, and
- when X is an oxygen atom, Y is a sulfur atom, $R_4$ and $R_5$ are hydrogen atoms, Z is a single bond and n is 1, then Ar must not be a phenyl group, their salts and solvates, and pharmaceutical compositions comprising said compounds.

BACKGROUND

With the recent change in the Japanese eating habits into Western-style ones to take high-calorie and high-cholesterol foods and drinks, which is based on the improvement in the living standard in Japan, and with the recent increase in the aged population of Japan, cases of hyperlipemia and arteriosclerotic disorders resulting from hyperlipemia are greatly increasing with bringing about one social problem in Japan. The conventional chemotherapy for cases of hyperlipemia and arteriosclerosis is essentially to lower their blood-lipid levels that participate in the disorders, but is not targeted to the focuses themselves of arteriosclerosis to cure them.

Acyl coenzyme A cholesterol acyltransferase (ACAT) is an enzyme to catalyze the transfer of cholesterol into cholesterol esters, while playing an important role in the metabolism of cholesterol and the absorption thereof through digestive systems. It is believed that the inhibition of such an ACAT enzyme that may catalyze the esterification of free cholesterol in epithelial cells in small intestines brings about the inhibition of the cholesterol absorption through intestinal tubes, while the inhibition of the formation of cholesterol esters in the liver based on the ACAT inhibition brings about the inhibition of the VLDL (very low-density lipoprotein) secretion into blood, thereby resulting in the decrease in the blood cholesterol. Many known ACAT inhibitors are expected to act on ACAT in small intestines and the liver as anti-hyperlipemic agents thereby to lower blood cholesterol.

For example, as ACAT inhibitors, U.S. Pat. No. 4,716,175 discloses 2,2-dimethyl-N-(2,4,6-trimethoxyphenyl) dodecanamide, and European Patent 372,445 discloses N'-(2,4-difluorophenyl)-N-[5-(4,5-diphenyl-1H-imidazol-2-ylthio)pentyl]-N-heptylurea. However, many known ACAT inhibitors have heretofore been specifically directed to the decrease in blood cholesterol as anti-hyperlipemic agents, and administered to patients in large amounts in order to express their effects. Therefore, in the clinical examination stage using them, many patients have experienced various side effects such as bleeding from the intestinal tubes, intestinal disorders, diarrhea and liver disorders, which have made it difficult to develop the clinical use of ACAT inhibitors.

WO92/09582 discloses compounds having a certain substituent at the 2-position of the imidazole skeleton; and EP-A 477,778 discloses compounds having certain substituents at the 4- and 5-positions of the imidazole skeleton. For example, disclosed are 5-[2-(2-(4-fluorophenyl)ethyl)-3-(1-methyl-1H-imidazol-2-yl)-2H-benzopyran-6-yl]oxy-2,2-dimethyl-N-(2,6-diisopropylphenyl)pentanamide (see WO92/09582), N-(2,6-diisopropylphenyl)-2-(tetradecylthio)acetamide (see JP 92-500533, WO92/09572), N-butyl-N'-[2-(3-(5-ethyl-4-phenyl-1-yl)propoxy)-6-methylphenyl]urea (see EP 477,778), and N-[5-(4,5-diphenyl-1H-imidazo-2-ylthio)pentyl]-N-heptyl-2-enzoxazolamine (see WO93/23392); and it is disclosed that these compounds have ACAT inhibiting activities. However, the chemical structures of these compounds are quite different from those of the compounds of the present invention.

3-(benzothiazol-2-ylthio)-N-(phenyl)propanamide, 3-(benzothiazol-2-ylthio)-N-(phenyl)ethanamide and 3-(benzothiazol-2-ylthio)-N-(p-chlorophenyl)ethanamide is reported in J. Chem. Eng. Data, 27, 207 (1982) and 3-(benzoxazol-2-ylthio)-N-(phenyl)propanamide is reported in Fungitsidy, Ed. Melnikov, N. N. Izd. Fan Uzb. SSR: Tashkent, USSR, 82–88 (1980).

SUMMARY

Naturally, arteriosclerosis is a disorder that is characterized by the increase in the thickness of intimate and the accumulation of lipids in blood vessels. The recent studies on this disorder, arteriosclerosis have clarified that the inhibition of macrophage-derived foam cells that play the central role in the formation of focuses of arteriosclerosis is expected to reduce the focuses themselves of arteriosclerosis. In the focuses of atheromatous arteriosclerosis, seen are macrophage-derived foam cells (which have fatty drops of cholesterol esters therein), and it is said that the formation of such foam cells from macrophages has close relation to the growth of the focuses of arteriosclerosis. In addition, it has been reported that the ACAT activity in the blood vessel walls in the site with arteriosclerotic lesions is increased and that cholesterol esters are accumulated on the blood vessel walls in said site (see Gillies, P. J., et al.; Exp. Mole. Pathol., 44, 329–339 (1986)).

Since the inhibition of the esterification of cholesterol by an ACAT inhibitor produces free cholesterol in cells while the resulting free cholesterol is removed from the cells by a high-density lipoprotein (HDL) and brought to the liver (countertransference of cholesterol via HDL) and metabolized therein, it is expected that such an ACAT inhibitor may inhibit the accumulation of cholesterol esters in the site of arteriosclerotic lesions. As a result, it is believed that ACAT inhibitors exhibit direct anti-arteriosclerotic effects. It has been reported that ACAT includes two sub-types, one existing in small intestines and the other existing in blood vessel walls (see Kinnunen, P. M., et al.; Biochem., 27, 7344–7350 (1988)). Many studies on ACAT inhibitors have heretofore been made for the former sub-type of ACAT existing in small intestines and the liver (see Tomoda, H. et al.; J. Antibiotics, 47, 148–153 (1994)). Having considered that chemicals capable of selectively inhibiting the latter sub-type of ACAT existing in blood vessel walls could be medicines with few side effects for curing arteriosclerosis, as compared with ACAT inhibitors not specific organs, we, the present inventors have searched for inhibitors for ACAT of that type and have studied to synthesize such ACAT inhibitors.

In order to attain this object, we have made various studies and, as a result, have found that compounds of a general formula (I):

$$\text{(I)}$$

(benzazole)—Y—(CH$_2$)$n$—C(R$_4$)(R$_5$)—Z—C(=O)—NH—Ar wherein
  Ar represents an optionally-substituted aryl group;
  R$_4$ and R$_5$ are the same or different, and each represents a hydrogen atom, a lower alkyl group, or a lower alkoxy group; and R$_4$ and R$_5$ may together form a lower alkylene group of which one or more methylene moieties may optionally be substituted by oxygen and/or sulfur atoms;
  X represents —NH—, or an oxygen or sulfur atom;
  Y represents —NH—, an oxygen or sulfur atom, or a sulfoxide or sulfone group;
  Z represents a single bond, or —NH$_6$—;
  R$_6$ represents a hydrogen atom or a lower alkylene group; and
  n is an integer of from 0 to 15;
  provided that, when X and Y are sulfur atoms, R$_4$ and R$_5$ are hydrogen atoms, Z is a single bond and n is 0, then Ar must not be a phenyl or p-chlorophenyl group,
  when X and Y are sulfur atoms, R$_4$ and R$_5$ are hydrogen atoms, Z is a single bond and n is 1, then Ar must not be a phenyl group, and
  when X is an oxygen atom, Y is a sulfur atom, R$_4$ and R$_5$ are hydrogen atoms, Z is a single bond and n is 1, then Ar must not be a phenyl group,
and their salts and solvates have excellent ACAT inhibiting activities. On the basis of these findings, we have completed the present invention.

We, the present inventors have found that some of those compounds have organ-selective, ACAT inhibiting activities and intracellular cholesterol transference inhibiting activities, as well as excellent blood cholesterol-reducing activities, and are therefore useful as anti-hyperlipemic agents, while some others have activities to inhibit the formation of foam cells from macrophages and are therefore especially useful as medicines for preventing and curing arteriosclerosis Accordingly, the present invention provides compounds of the above-mentioned formula (I), and their salts and solvates.

In addition, the present invention also provides pharmaceutical compositions comprising any of compounds of the above-mentioned formula (I) and their salts and solvates, along with pharmaceutically-acceptable carriers.

The present invention further provides ACAT inhibitors, intracellular cholesterol transference inhibitors, blood cholesterol depressants, and inhibitors for macrophage foam cells, which comprise compounds of a general formula (III):

$$\text{(III)}$$

(benzazole)—Y—(CH$_2$)$n$—C(R$_4$)(R$_5$)—Z—C(=O)—NH—Ar where
  Ar represents an optionally-substituted aryl group;
  R$_4$ and R$_5$ are the same or different, and each represents a hydrogen atom, a lower alkyl group, or a lower alkoxy group; and R$_4$ and R$_5$ may together form a lower alkylene group of which one or more methylene moieties may optionally be substituted by oxygen and/or sulfur atoms;
  X represents —NH—, or an oxygen or sulfur atom;
  Y represents —NH—, an oxygen or sulfur atom, or a sulfoxide or sulfone;
  Z represents a single bond, or —NH$_6$—;
  R$_6$ represents a hydrogen atom or a lower alkylene group; and
  n is an integer of from 0 to 15;
and their pharmaceutically-acceptable salts and solvates, optionally along with pharmaceutically-acceptable carriers. Specifically, the present invention provides medicines for treating, preventing and curing disorders of, for example, hyperlipemia, arteriosclerosis, cervical and cerebral arteriosclerosis, cerebrovascular disorders, ischemic cardiopathy, coronary arteriosclerosis, nephrosclerosis, arteriosclerotic nephrosclerosis, arteriolosclerotic nephrosclerosis, malignant nephrosclerosis, ischemic enterophathy, acute mesenteric vaso-obstruction, chronic intestinal angina, ischemic colitis, aortic aneurysm, and arteriosclerosis obliterans (ASO), which medicines comprise any of compounds of the above-mentioned formula (III) and their pharmaceutically-acceptable salts and solvates, optionally along with pharmaceutically-acceptable carriers.

The present invention further provides a method for treatments using an ACAT inhibitor, an intracellular cholesterol transference inhibitor, a blood cholesterol depressant, or an anti-foaming agent for macrophages, which comprises an effective dosage of any of compounds of a general formula (III) and their salts and solvates.

The present invention provides further also use for the preparation of medicines using an ACAT inhibitor, an intracellular cholesterol transference inhibitor, a blood cholesterol depressant, or an anti-foaming agent for macrophages, which comprises an effective dosage of any of compounds of a general formula (III) and their salts and solvates.

The aryl group for Ar in formula (I) may include a phenyl group, an α-naphthyl group and a β-naphthyl group, and is preferably a phenyl group. The group Ar may be substituted by any substituents not having any negative influence on the ACAT inhibiting activities of compounds (I). Preferred substituents for Ar are, for example, a lower alkyl group, a lower alkoxy group, a halogen atom, a hydroxyl group, a phosphoric acid group, a sulfonamido group, and an optionally-substituted amino group. Especially preferred are a lower alkyl group, a lower alkoxy group an a halogen atom.

More precisely, the present invention provides compounds of a formula (II):

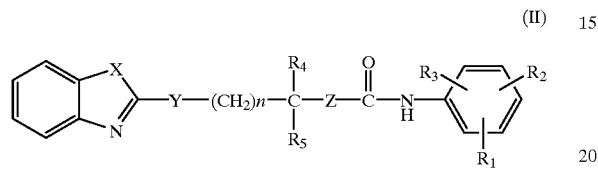
(II)

where $R_1$, $R_2$ and $R_3$ are the same or different, and each represents a hydrogen atom, a lower alkyl group, a lower alkoxy group, a halogen atom, a hydroxyl group, a phosphoric acid group, a sulfonamido group, or an optionally-substituted amino group; or any two of $R_1$, $R_2$ and $R_3$ together form an alkylenedioxy group; $R_4$ and $R_5$ are the same or different, and each represents a hydrogen atom, a lower alkyl group, or a lower alkoxy group; and $R_4$ and $R_5$ may together form a lower alkylene group of which one or more methylene moieties may optionally be substituted by oxygen and/or sulfur atoms;

X represents —NH—, or an oxygen or sulfur atom;

Y represents —NH—, an oxygen or sulfur atom, or a sulfoxide or sulfone;

Z represents a single bond, or —NH$_6$—;

$R_6$ represents a hydrogen atom or a lower alkylene group; and n is an integer of from 0 to 15;

provided that, when X is an oxygen or sulfur atom, Y is a sulfur atom, Z is a single bond and n is 0 or 1, then all $R_1$ to $R_5$ must not be hydrogen atoms at the same time, and when X and Y are sulfur atoms, $R_4$ and $R_5$ are hydrogen atoms, Z is a single bond and n is 0, then $R_1$ to $R_3$ must not be such that any one of these is a para-positioned chlorine atoms while the other two are hydrogen atoms, and their salts and solvates.

In addition, the present invention also provides pharmaceutical compositions comprising any of compounds of the above-mentioned formula (II) and their salts and hydrates, along with pharmaceutically-acceptable carriers.

The present invention further provides ACAT inhibitors, intracellular cholesterol transference inhibitors, blood cholesterol depressants, and inhibitors for macrophage foam cells, which comprise anilide compounds of a formula (IV):

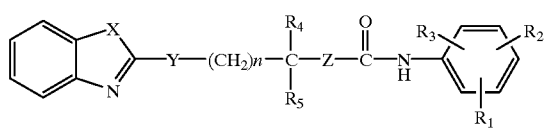
(IV)

wherein $R_1$, $R_2$ and $R_3$ are the same or different, and each represents a hydrogen atom, a lower alkyl group, a lower alkoxy group, a halogen atom, a hydroxyl group, a phosphoric acid group, a sulfonamido group, or an optionally-substituted amino group; or any two of $R_1$, $R_2$ and $R_3$ together form an alkylenedioxy group; $R_4$ and $R_5$ are the same or different, and each represents a hydrogen atom, a lower alkyl group, or a lower alkoxy group; and $R_4$ and $R_5$ may together form a lower alkylene group of which one or more methylene moieties may optionally be substituted by oxygen and/or sulfur atoms;

X represents —NH—, or an oxygen or sulfur atom;

Y represents —NH—, an oxygen or sulfur atom, or a sulfoxide or sulfone group;

Z represents a single bond, or —NH$_6$—;

$R_6$ represents a hydrogen atom or a lower alkylene group; and n is an integer of from 0 to 15;

and their pharmaceutically-acceptable salts and solvates, optionally along with pharmaceutically-acceptable carriers. Specifically, the present invention provides medicines for treating, preventing and curing disorders of, for example, hyperlipemia, arteriosclerosis, cervical and cerebral arteriosclerosis, cerebrovascular disorders, ischemic cardiopathy, coronary arteriosclerosis, nephrosclerosis, arteriosclerotic nephrosclerosis, arteriolosclerotic nephrosclerosis, malignant nephrosclerosis, ischemic enteropathy, acute mesenteric vaso-obstruction, chronic intestinal angina, ischemic colitis, aortic aneurysm, and arteriosclerosis obliterans (ASO), which medicines comprise any of compounds of the above-mentioned formula (IV) and their pharmaceutically-acceptable salts and hydrates, optionally along with pharmaceutically-acceptable carriers.

The lower alkyl group as referred to herein is a linear or branched one having from 1 to 8 carbon atoms, preferably from 1 to 6 carbon atoms, and includes, for example, a methyl group, an ethyl group, a n-propyl group, an iso-propyl group, an n-butyl group, an iso-butyl group, a tert-butyl group, a n-pentyl group, and a n-hexyl group. The alkyl moiety in the lower alkoxy group as referred to herein is preferably an alkyl group such as that mentioned hereinabove. The halogen atom is preferably a fluorine, chlorine, bromine, or iodine atom. The amino group may optionally be substituted with 1 or 2 substituents. As the substituents for the amino group, preferred are a lower alkyl group such as that mentioned hereinabove; an aryl group such as phenyl or naphthyl group; and an aralkyl group such as a benzyl or phenethyl group. The aromatic ring in these substituents may further be substituted with any of lower alkyl groups and lower alkoxy groups such as those mentioned hereinabove.

The alkylenedioxy group as referred to herein comprises a linear or branched alkylene group having from 1 to 8 carbon atoms, preferably from 1 to 5 carbon atoms, and has two oxygen atoms as inserted into any desired sites including the both terminals of said alkylene moiety. For example, the group includes a methylenedioxy group and an ethylenedioxy group.

The lower alkyl group for $R_5$ and $R_6$ is preferably one to be selected from those mentioned hereinabove. The lower alkylene group to be formed by $R_4$ and $R_5$ is a linear or branched one having from 1 to 8 carbon atoms, preferably from 2 to 5 carbon atoms, and includes, for example, a methylene group (this forms a vinyl group together with the adjacent carbon atom), a propylene group, a butylene group, and a pentylene group. Of the alkylene group, one or more methylene moieties (each comprising one carbon atom and two hydrogen atoms) may be substituted with oxygen and/or sulfur atoms.

Acid addition salts of compounds (I) of the invention include, for example, inorganic acid salts thereof, such as hydrochlorides, sulfates, nitrates and phosphates; and organic acid salts thereof, such as methanesulfonates, maleates, fumarates, and citrates.

The solvates include, for example, those with solvents used in the production or purification of compounds (I), such as water or alcohols, and the solvents are not specifically defined provided that they do not have any negative influence on the ACAT inhibiting activities of the resulting solvates. As the solvates, preferred are hydrates.

MODES OF CARRYING OUT THE INVENTION

Compounds of formulae (I), (II), (III) and (IV) can be produced by any known methods, and the production of said compounds shall not be specifically defined. For example, they can be produced according to the following methods.

1. Method of producing compounds having a single bond as Z:

Compounds of formulae (I), (II), (III) and (IV) having a single bond as Z can be produced by reacting a carboxylic acid or its reactive derivative of a general formula (V) with an aniline derivative of a general formula (VI) an then with a 2-substituted benzazole derivative of a general formula (VIII) in that order.

(1) According to the reaction steps mentioned below, a carboxylic acid or its reactive derivative, such as its halide, of formula (V) is reacted with an aniline derivative of formula (VI) to give an amide derivative of a general formula (VII). The resulting derivative (VII) is reacted with a 2-substituted benzazole compound of formula (VIII) to give the intended compound having a single bond as Z.

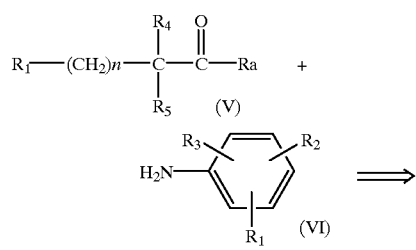

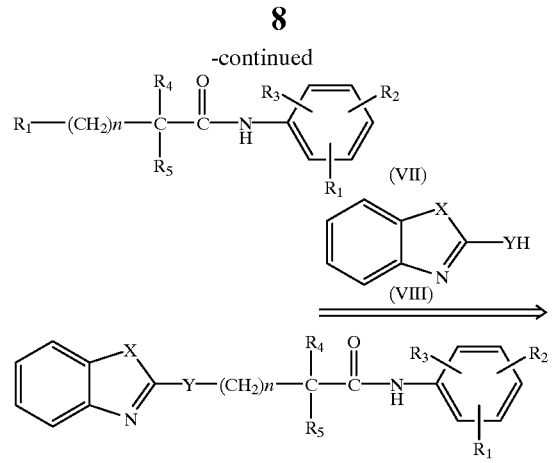

wherein $R_7$ represents a removable group; and $R_8$ represents a hydroxyl group, or a residue of a reactive derivative for the carboxyl group.

To the reaction of the compound (V) and the compound (VI), applicable is any ordinary means of peptide synthesis. For example, the two compounds are reacted in the presence of a condensing agent to give the intended compound. As the condensing agent, for example, 1-(3'-dimethylaminopropyl)-3-ethylcarbodiimide (WSC) or 1,3-dicyclohexylcarbodiimide (DCC) can be used singly. If desired, said condensing agent can be combined with a condensation activator, such as 1-hydroxybenzotriazole (HOBt) or N-hydroxysuccinimide (HOSu). The solvent for the reaction is not specifically defined. For example, usable are dimethylformamide (DMF), methylene chloride, chloroform, tetrahydrofuran and toluene, either singly or as combined. The reaction mode varies, depending on the starting compounds used. In general, however, the starting compounds are reacted with cooling with ice or at higher temperatures but up to the boiling point of the solvent used, for example, at from 0 to 100° C., preferably at about room temperature, for from 1 to 30 hours, preferably for from 10 to 20 hours, to finish the reaction. If a highly-reactive carboxylic acid halide is used as the starting compound (V), for example, it may be reacted with the compound (VI) in the presence of a base, such as triethylamine, 4-dimethylaminopyridine or N-methylmorpholine, in any ordinary manner. The starting compounds (V) and (VI) are known compounds. For example, the compounds (V) can be obtained through oxidation of a haloalkyl alcohol with a Jones' reagent or the like into the corresponding carboxylic acid. The compounds (VI) can be obtained through catalytic reduction of a nitrobenzene derivative into the corresponding aniline derivative.

The reaction of the compound (VII) as obtained in the above-mentioned step and the compound (VIII) may be effected in a solvent in the presence or absence of abase. As the solvent, usable is any of those mentioned above. The base usable herein includes inorganic bases, for example, alkali metal hydroxides such as sodium hydroxide and potassium hydroxide; alkali metal carbonates such as sodium carbonate and potassium carbonate; and alkali metal hydrogencarbonates such as sodium hydrogencarbonate and potassium hydrogencarbonate; as well as organic bases such as pyridine, triethylamine, N,N-diisopropylethylamine, N-methylmorpholine and N,N-dimethylaniline.

(2) Alternatively, according to the reaction steps mentioned below, a 2-substituted benzazole compound of formula (VIII) is reacted with a free carboxylic acid of formula (V) or its derivative as inactivated at its carboxyl moiety to give a benzazole-substituted carboxylic acid derivative of formula (IX). The resulting compound or its reactive derivative, such as its acid halide, of formula (IX) is reacted with an aniline derivative of formula (VI) to give the intended compound having a single bond as Z.

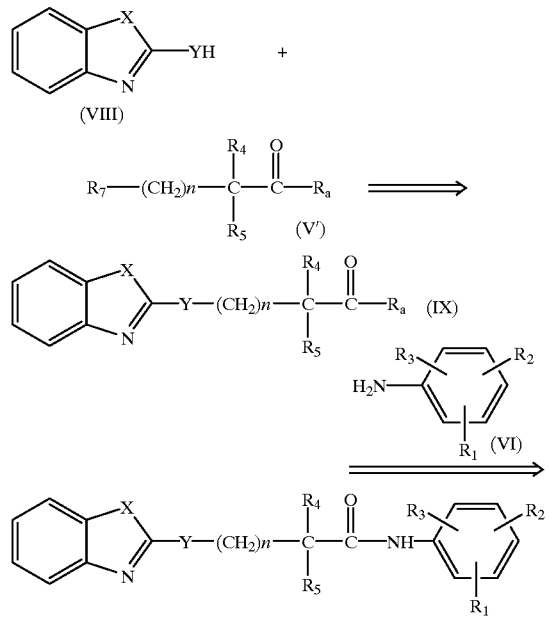

wherein $R_7$ represents a removable group; and $R_9$ represents a hydroxyl group, or a residue of a derivative for the carboxyl group.

The reaction of the compound (VIII) and the compound (V') can be effected in accordance with the second step of the above-mentioned method (1). For this, it is especially desirable to use potassium hydroxide as the base and ethanol as the solvent. The next reaction of the compound (IX) and the compound (VI) can be effected in accordance with the first step of the above-mentioned method (1).

2. Method of producing compounds having —$NR_6$— as Z:

(1) Method of producing compounds having hydrogen atom as $R_6$.

Compounds (I), (II), (III) and (IV) where $R_6$ is hydrogen atom, and is, Z is —NH—, may be produced according to various methods. One example comprises the following reaction steps.

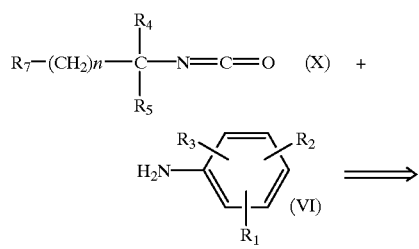

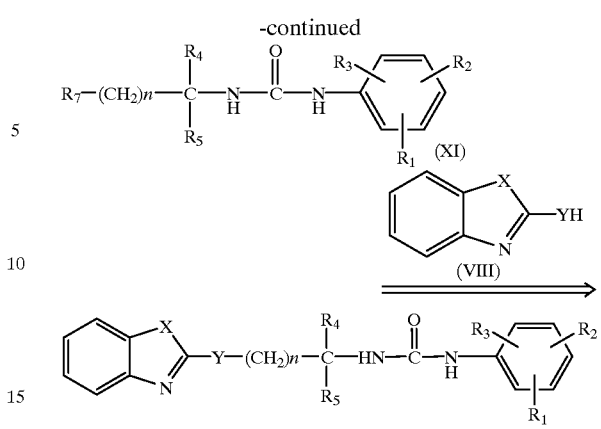

wherein $R_7$ represents a removing group.

An isocyanate derivative of formula (X) is reacted with an aniline derivative of formula (VI) to give an urea derivative of formula (XI). The resulting urea derivative (XI) is reacted with a 2-substituted benzazole derivative of formula (VIII) to give the intended compound having —$NR_6$— as Z.

In the first step, the compound (X) is reacted with from 1 to 2 equivalents, relative to the compound (X), of the compound (VI) in a solvent to give the compound (XI). The solvent is not specifically defined, but is preferably any of methylene chloride, chloroform, hexane, ether, tetrahydrofuran, toluene, xylene or dimethylformamide. The reaction is effected at from 0° C. to the boiling point of the solvent used, for from 1 to 24 hours. The isocyanate derivatives (X) are known compounds, and can be produced, for example, according to a process comprising reacting a carboxylic acid of formula (V) with diphenylphosphoryl azide in the presence of a base (Shioiri et al's process); or according to a process comprising reacting an acid halide of formula (V) with sodium azide to give an acid azide. The reaction of the compound (XI) and the compound (VIII) may be effected in accordance with the second step of the above-mentioned method 1-(1).

(2) Method of producing compounds having lower alkyl group as $R_6$.

Compounds (I), (II), (III) and (IV) where $R_6$ is lower alkyl group may be produced according to various methods. One example comprises the following reaction steps.

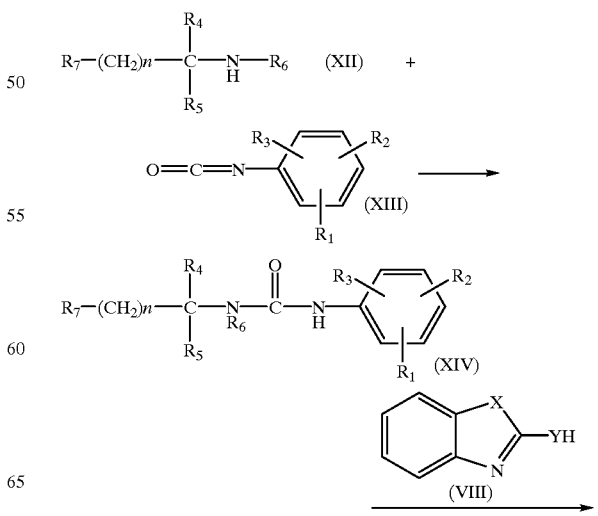

-continued

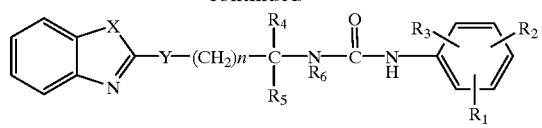

wherein $R_7$ represents a removing group.

An isocyanate derivative of formula (XIII) is reacted with an secondary amine shown as formula (XII) to give an urea derivative of formula (XIV). The resulting urea derivative is reacted with a 2-substituted benzazole derivative of formula (VIII) to give the intended compound having lower alkyl group as $R_4$ in Z.

The reaction between the compound (XII) and the compounds (XIII) in the first step may be performed accordance with the reaction between isocyanate derivatives (X) and aniline derivatives (VI) mentioned above, and the reaction between the compounds (XIV) and the compounds (VIII) may be performed accordance with the reaction between amide derivatives (VII) and benzazole compounds (VIII) mentioned above.

Secondary amines shown as the formula (XII) are known compounds, and they may be produced by that amide which is obtained from condensing firstly aminoalcohol and alkylcarbonic acid is reduced.

Also, isocyanate derivatives of the compounds (XIII) may be produced by known methods, for example, the method that corresponded aniline derivatives are made to isocyanate with the one known method using hosgen and so on.

The intermediates and the final compounds obtained in the reaction steps in the above-mentioned methods can be isolated and purified through ordinary purification in organic synthetic chemistry, which includes, for example, filtration, extraction, washing, drying, concentration, recrystallization, and various chromatographic means. For the intermediates, they can be used in the next reaction step without being specifically purified.

In the methods illustrated hereinabove, used are aniline derivatives of formula (VI) as the amines to form the amine moiety in the amido group of the compounds of the present invention. However, it is obvious to those skilled in the art that, when arylamine derivatives are used in place of said aniline derivatives, compounds of formulae (I) and (III) of the present invention can be produced.

The compounds of formulae (I), (II), (III) and (IV) thus obtained can be converted into their acid addition salts in any ordinary manner.

If desired, they can be obtained as their solvates, especially their hydrates, with solvents such as those used for reaction or recrystallization.

Specific examples of the compounds of formulae (I), (II), (III) and (IV) obtainable according to the methods mentioned hereinabove are in the following Table 1 to Table 4.

TABLE 1

| Ex. | X | Y | Z | n | R1 | R2 | R3 | R4 | R5 |
|---|---|---|---|---|---|---|---|---|---|
| 1 | O | S | single bond | 0 | 2-iPr | H | 6-iPr | H | H |
| 2 | O | S | single bond | 1 | 2-iPr | H | 6-iPr | H | H |
| 3 | O | S | single bond | 2 | 2-iPr | H | 6-iPr | H | H |
| 4 | O | S | single bond | 3 | 2-iPr | H | 6-iPr | H | H |
| 5 | O | S | single bond | 4 | 2-iPr | H | 6-iPr | H | H |

TABLE 1-continued

| Ex. | X | Y | Z | n | R1 | R2 | R3 | R4 | R5 |
|---|---|---|---|---|---|---|---|---|---|
| 6 | O | S | single bond | 5 | 2-iPr | H | 6-iPr | H | H |
| 7 | O | S | single bond | 6 | 2-iPr | H | 6-iPr | H | H |
| 8 | O | S | single bond | 7 | 2-iPr | H | 6-iPr | H | H |
| 9 | O | S | single bond | 8 | 2-iPr | H | 6-iPr | H | H |
| 10 | O | S | single bond | 13 | 2-iPr | H | 6-iPr | H | H |
| 11 | O | S | single bond | 0 | 2-F | H | 4-F | H | H |
| 12 | O | S | single bond | 2 | 2-F | H | 4-F | H | H |
| 13 | O | S | single bond | 3 | 2-F | H | 4-F | H | H |
| 14 | O | S | single bond | 4 | 2-F | H | 4-F | H | H |
| 15 | O | S | single bond | 8 | 2-F | H | 4-F | H | H |
| 16 | O | S | single bond | 3 | 2-iPr | H | 6-iPr | Me | Me |
| 17 | O | S | single bond | 4 | 2-iPr | H | 6-iPr | —(CH2)4— | |
| 18 | O | S | single bond | 4 | 2-iPr | H | 6-iPr | —(CH2)3— | |
| 19 | O | S | single bond | 4 | 2-iPr | H | 6-Me | H | H |
| 20 | O | S | single bond | 4 | 3-OMe | 4-OMe | 5-OMe | H | H |
| 21 | O | S | single bond | 4 | 2-iPr | H | 6-iPr | H | H |
| 22 | O | S | single bond | 4 | 2-iPr | H | 6-iPr | H | H |

TABLE 2

| Ex. | X | Y | Z | n | R1 | R2 | R3 | R4 | R5 |
|---|---|---|---|---|---|---|---|---|---|
| 23 | N | S | single bond | 0 | 2-iPr | H | 6-iPr | H | H |
| 24 | N | S | single bond | 2 | 2-iPr | H | 6-iPr | H | H |
| 25 | N | S | single bond | 3 | 2-iPr | H | 6-iPr | H | H |
| 26 | N | S | single bond | 4 | 2-iPr | H | 6-iPr | H | H |
| 27 | N | S | single bond | 5 | 2-iPr | H | 6-iPr | H | H |
| 28 | N | S | single bond | 6 | 2-iPr | H | 6-iPr | H | H |
| 29 | N | S | single bond | 7 | 2-iPr | H | 6-iPr | H | H |
| 30 | N | S | single bond | 8 | 2-iPr | H | 6-iPr | H | H |
| 31 | N | S | single bond | 13 | 2-iPr | H | 6-iPr | H | H |
| 32 | N | S | single bond | 0 | 2-F | H | 4-F | H | H |
| 33 | N | S | single bond | 2 | 2-F | H | 4-F | H | H |
| 34 | N | S | single bond | 3 | 2-F | H | 4-F | H | H |
| 35 | N | S | single bond | 4 | 2-F | H | 4-F | H | H |
| 36 | N | S | single bond | 8 | 2-F | H | 4-F | H | H |
| 37 | N | S | single bond | 3 | 2-iPr | H | 6-iPr | Me | Me |
| 38 | N | S | single bond | 4 | 2-iPr | H | 6-Me | H | H |
| 39 | N | S | single bond | 4 | 3-OMe | 4-OMe | 5-OMe | H | H |

TABLE 2-continued

| Ex. | X | Y | Z | n | R1 | R2 | R3 | R4 | R5 |
|---|---|---|---|---|---|---|---|---|---|
| 40 | N | SO | single bond | 4 | 2-iPr | H | 6-iPr | H | H |
| 41 | N | SO2 | single bond | 4 | 2-iPr | H | 6-iPr | H | H |

TABLE 3

| Ex. | X | Y | Z | n | R1 | R2 | R3 | R4 | R5 |
|---|---|---|---|---|---|---|---|---|---|
| 42 | S | S | single bond | 0 | 2-iPr | H | 6-iPr | H | H |
| 43 | S | S | single bond | 1 | 2-iPr | H | 6-iPr | H | H |
| 44 | S | S | single bond | 2 | 2-iPr | H | 6-iPr | H | H |
| 45 | S | S | single bond | 3 | 2-iPr | H | 6-iPr | H | H |
| 46 | S | S | single bond | 4 | 2-iPr | H | 6-iPr | H | H |
| 47 | S | S | single bond | 5 | 2-iPr | H | 6-iPr | H | H |
| 48 | S | S | single bond | 6 | 2-iPr | H | 6-iPr | H | H |
| 49 | S | S | single bond | 7 | 2-iPr | H | 6-iPr | H | H |
| 50 | S | S | single bond | 8 | 2-iPr | H | 6-iPr | H | H |
| 51 | S | S | single bond | 13 | 2-iPr | H | 6-iPr | H | H |
| 52 | S | S | single bond | 0 | 2-F | H | 4-F | H | H |
| 53 | S | S | single bond | 2 | 2-F | H | 4-F | H | H |
| 54 | S | S | single bond | 3 | 2-F | H | 4-F | H | H |
| 55 | S | S | single bond | 4 | 2-F | H | 4-F | H | H |
| 56 | S | S | single bond | 8 | 2-F | H | 4-F | H | H |
| 57 | S | S | single bond | 3 | 2-iPr | H | 6-iPr | Me | Me |
| 58 | S | S | single bond | 4 | 2-iPr | H | 6-Me | H | H |
| 59 | S | S | single bond | 4 | 3-OMe | 4-OMe | 5-OMe | H | H |

TABLE 4

| Ex. | X | Y | Z | n | R1 | R2 | R3 | R4 | R5 |
|---|---|---|---|---|---|---|---|---|---|
| 60 | O | S | —NH— | 1 | 2-iPr | H | 6-iPr | H | H |
| 61 | O | S | —NH— | 3 | 2-iPr | H | 6-iPr | H | H |
| 62 | O | S | —NH— | 6 | 2-iPr | H | 6-iPr | H | H |
| 63 | S | S | —NH— | 1 | 2-iPr | H | 6-iPr | H | H |
| 64 | O | S | —NH— | 1 | 2-F | H | 4-F | H | H |
| 65 | O | S | —NH— | 3 | 2-F | H | 4-F | H | H |
| 66 | O | S | single bond | 7 | 2-iPr | H | 6-iPr | H | H |
| 67 | O | S | single bond | 7 | 2-iPr | H | 6-iPr | H | H |
| 68 | O | S | single bond | 0 | F | F | F | H | H |
| 69 | O | S | single bond | 4 | F | F | F | H | H |
| 70 | O | S | single bond | 7 | F | F | F | H | H |
| 71 | O | S | —NR— | 7 | 2-iPr | H | 6-iPr | H | H |

Remarks: R is represented by heptyl.

Compounds of formulae (III) and (IV) of the present invention have ACAT inhibiting activities and/or intracellular cholesterol transference inhibiting activities, and are useful as medicines for curing and treating hyperlipemia and those for curing and treating arteriosclerosis in the field of medicine. In particular, since the compounds of the present invention act to selectively inhibit a sub-type of ACAT enzyme existing in blood vessel walls, they are expected to have less side effects than non-selective ACAT inhibitors. Thus, the compounds of the invention are favorable as active ingredients in medicines.

The pharmaceutical composition of the present invention comprises, as the active ingredient, any of compounds of formulae (III) and (IV) and their acid addition salts and solvates, either singly or along with any other pharmaceutically-acceptable excipients, binders, carriers or diluents, and can be formulated into various preparations such as tablets, capsules, granules, powders, injections and suppositories. To formulate these preparations, employable are any known methods. For example, to formulate oral preparations, the active ingredient of compounds (III) and (IV) is combined with an excipient such as starch, mannitol or lactose; a binder such as sodium carboxymethyl cellulose or hydroxypropyl cellulose; a disintegrator such as crystalline cellulose or calcium carboxymethyl cellulose; a lubricant such as talc or magnesium stearate; and a flowability improver such as light silicic anhydride.

The pharmaceutical composition of the present invention is administered to patients either orally or parenterally.

The dose of the pharmaceutical composition of the invention shall vary, depending on the body weight, the age, the sex and the condition of the patient. Preferably, however, the dose is generally from 1 to 1000 mg/adult/day, more preferably from 5 to 200 mg/adult/day, in terms of the active ingredient of compounds (III) and (IV) existing in the composition, and the composition of said dose is administered once to three times a day.

The following Test Example is to demonstrate the ACAT inhibiting activities of compounds of formulae (III) and (IV) of the invention.

Test Example 1

Rabbits were fed with 1% cholesterol feed for 8 weeks. Microsomes were prepared from the thoracoaorta of the rabbits in an ordinary manner, and suspended in 0.15 M phosphate buffer (pH 7.4) to prepare blood vessel wall-derived enzyme liquids. Small intestine-derived enzyme liquids were prepared from the small intestines of rabbits fed with ordinary feed. To determine the ACAT inhibiting activities of test compounds, employed herein was a modified method of J. G. Heider (see J. Lipid Res., 24, 1127–1134, 1983). Briefly, 2 $\mu$l of a test compound as dissolved in dimethylsulfoxide (DMSO) was added to 88 $\mu$l of 0.15 M phosphate buffer (pH 7.4) containing $^{14}$C-oleoyl-CoA (40 $\mu$M, 60000 dpm) and bovine serum albumin (2.4 mg/ml), and incubated therein at 37° C. for 5 minutes. 10 $\mu$l of the enzyme liquid was added to the resulting solution and reacted at 37° C. for 5 minutes (for small intestine-derived enzyme liquids, for 3 minutes), and thereafter 3 ml of chloroform/methanol (2/1) and 0.5 ml of 0.04 N HCl were added thereto to stop the reaction. After the reaction, lipids were extracted from the reaction mixture. The solvent layer was concentrated to dryness, then dissolved in hexane, spotted on a TLC plate (produced by Merck), and developed thereon with a developer of hexane/ether/acetic acid (75/25/1). The radioactivity of the thus-fractionated cholesterol ester fraction was measured with BAS2000 (produced by Fuji Film). Comparing the data with those of the control to which had been added only DMSO, $IC_{50}$ was obtained. The results are shown in Table 5.

TABLE 5

| Test Compound (Example No.) | Blood Vessel Wall-Derived Enzyme $IC_{50}$ ($\mu$M) | Small Intestine-Derived Enzyme $IC_{50}$ ($\mu$M) | $IC_{50}$ (Small Intestine)/$IC_{50}$ (blood vessel walls) |
|---|---|---|---|
| 1 | 0.035 | 0.200 | 5.71 |
| 2 | 0.015 | 0.025 | 1.67 |
| 3 | 0.010 | 0.065 | 6.50 |
| 5 | 0.010 | 0.065 | 6.50 |
| 8 | 0.004 | 0.021 | 4.77 |
| 15 | 1.2 | 2.9 | 2.42 |
| 23 | 2.3 | 5.8 | 2.52 |
| 36 | 1.4 | 9.1 | 6.50 |
| 44 | 0.028 | 0.10 | 3.57 |
| 57 | 0.21 | 0.27 | 1.29 |
| 61 | 0.27 | 0.13 | 0.48 |
| Control (1) | 0.45 | 0.87 | 1.93 |
| Control (2) | 0.033 | 0.019 | 0.58 |

TABLE 5-continued

| Test Compound (Example No.) | Blood Vessel Wall-Derived Enzyme $IC_{50}$ ($\mu$M) | Small Intestine-Derived Enzyme $IC_{50}$ ($\mu$M) | $IC_{50}$ (Small Intestine)/$IC_{50}$ (blood vessel walls) |
|---|---|---|---|
| Control (3) | 0.20 | 0.037 | 0.19 |
| Control (4) | 0.026 | 0.037 | 1.42 |

As comparative compounds, 5-[2-(2-(4-fluorophenyl)ethyl)-3-(1-methyl-1H-imidazol-2-yl)-2H-benzopyran-6-yl]oxy-2,2-dimethyl-N-(2,6-diisopropylphenyl)pentanamide described in WO92/09582 (control (1)), N-(2,6-diisopropylphenyl)-2-(tetradecylthio)acetamide described in WO92/09572 (control (2)), N-butyl-N-[2-{3-(5-ethyl-4-phenyl-1H-imidazol-1-yl)propoxy}-6-methylphenyl]urea described in EP-A 477,778 (control (3)), and N-[5-(4,5-diphenyl-1H-imidazol-2-ylthio)pentyl]-N-heptyl-2-benzoxazolamine described in WO93/23392 (control (4)) were tested in the same manner as above, and the data obtained are also shown in Table 5.

Test Example 2

Deterioration Action of Cholesterol

A deterioration action of cholesterol in plasma was treated with BIO $F_1B$ hybrid syrian hamster (Mark C. K. et al., Atheorosclerosis, 91 (1991) 35–40: abbreviated as $F_1B$ hamster in the following) which has an accumulation of cholesterol in blood vessel by cholesterol load. That is, 4 groups of $F_1B$ hamster (male, 8 weeks old, about 100 g weight) were made, which had five hamsters respectively, and the hamsters were fed with the below-described feeds corresponding to each group for 4 weeks. At the 4th week from beginning feed, blood of the hamsters were drewn from their jugulars; and values of total cholesteroles in plasma were measured with the enzyme method. The results are shown in Table 6.

TABLE 6

| Dosaged Group | Total Cholestrol in Plasma (mg/dl) | | inhibiting an increase (%) |
|---|---|---|---|
| | Before Dosage | At the 4th week | |
| (1) | 148.8 ± 7.1 | 255.5 ± 15.6 | * |
| (2) | 158.0 ± 7.7 | 987.0 ± 34.2 | * |
| (3) | 155.5 ± 10.1 | 398.3 ± 64.3 | 80.5 |
| (4) | 164.3 ± 8.8 | 170.1 ± 18.5* | 111.7 |

The group (1), (2), (3) and (4) in the Table 6 means followings.

(1) Group of Ordinal Foods: CE-2 (produced by Nihon Kurea Co.).
(2) Group of Hyperfat Foods: Added 0.05% cholesterol & 10% coconut oil to ordinal Foods.
(3) 1st Group of Tested Substances: Added 0.03% compound of Example 8 to the hyperfat foods.
(4) 2nd Group of Tested Substances: Added 0.3% compound of Example 8 to the hyperfat foods.

The mark * in Table 6 means p<0.01 (the significant difference to the group of hyperfat foods by Dunnett examination.). The ratio of inhibiting an increase was calculated with the following formula.

The ratio of inhibiting an increase (%) =

$$\frac{((\text{Group of Hyperfat}) - (\text{Group of Tested Substance}))}{((\text{Group of Hyperfat}) - (\text{Group of Ordinal Foods}))} \times 100$$

Test Example 3

ACAT inhibiting activities in J774 cell and HepG2 cell (Anti-foaming activities).

J774 cell and HepG2 cell were sown on 24-holes-plates, and J774 cell was cultured with DMEM culturing solution (including 10% fetal bovine serum), and HepG2 cell was cultured with MEM culturing solution (including 10% fetal bovine serum), and they were incubated with 5% $CO_2$ at 37° C. for 24 hours. And then each culturing solutions was changed to 0.5 ml of the culturing solution including 10 $\mu$g/ml of 25-OH cholesterol and specimen, and each cell was further cultured for 18 hours. After removing the medium, each cultured cell was washed with PBS two times, and then extracted with 1.5 ml of hexane:iso-propanol (3:2), and concentrated and dried. Each extracted substance was solved into iso-propanol including 0.2 ml of 10% Triton X-100. And total cholesterol (TC) of each was measured with Cholesterol E Test Wako (Wako Junyaku Co.,), and free cholesterol (FC) of each was measured with Free Cholesterol E Test Wako (Wako Junyaku Co.). The residue of extracting was dissolved with 0.25 ml of 2N NaOH at 37° C. for 30 minutes, and an amount of protein was measured with BCA Protein Assay Reagent (Pierce). The amount of cholesterol ester per protein was calculated based on a difference between TC and FC, and $IC_{50}$ was calculated in contrast with control. The results are shown in Table 7.

TABLE 7

| Test Compound (Example No.) | J 774 Cell-Derived Enzyme $IC_{50}$ ($\mu$M) | HepG 2-Dervied Enzyme $IC_{50}$ ($\mu$M) | $IC_{50}$ (HepG 2)/$IC_{50}$ (J 774) |
|---|---|---|---|
| 1 | 1.2 | 1.0 | 0.83 |
| 2 | 0.47 | 1.2 | 2.55 |
| 5 | 1.9 | 1.6 | 0.84 |
| 6 | 0.31 | 8.1 | 26.13 |
| 8 | 0.007 | 0.61 | 87.14 |
| 23 | 2.2 | 12 | 5.45 |
| 44 | 5.6 | 2.1 | 0.38 |
| Control (1) | 0.56 | 5.3 | 9.46 |
| Control (2) | 0.15 | 1.4 | 9.33 |
| Control (4) | 0.12 | 0.75 | 6.25 |

** Controls (1), (2) and (4) are the same as controls of Test Example 1.

As the above-mentioned results, the compounds of the present invention has the superior inhibition for ACAT, in particular, since the compounds of the present invention act to selectively inhibit a sub-type of the ACAT enzyme existing in blood vessel wall, it is found that they are expected as medicines for curing arteriousclerosis which have less side effects than non-selective ACAT inhibitions. And also, the compounds of the present invention has an activity to deteriorate cholesterol, which depends on dose.

EXAMPLES

The following examples are to demonstrate the compounds of the present invention, which, however, are not intended to restrict the scope of the invention.

Example 1

Production of 2-(benzoxazol-2-ylthio)-N-(2,6-diisopropylphenyl)acetamide:

1-(3'-Dimethylaminopropyl)-3-ethylcarbodiimide hydrochloride (WSC) (2.1 g, 11 mmols) and 1-hydroxybenzotriazole (HOBt) (1.49 g, 11 mmols) were added to an N,N-dimethylformamide (DMF) (30 ml) solution of 2,6-diisopropylaniline (1.97 g, 10 mmols) and bromoacetic acid (2.08 g, 15 mmols), and stirred at room temperature for 12 hours. The reaction mixture was extracted with ethyl acetate. The organic layer was washed with water, 1 N HCl, an aqueous saturated solution of sodium hydrogencarbonate and saturated saline in that order, and dried with anhydrous magnesium sulfate, and the solvent was evaporated. Then, the residue was purified through silica gel column chromatography (developer: hexane/acetone=5/1), and the resulting crystals were recrystallized from ether-hexane to obtain 1.26 g (42%) of 2-bromo-N-(2,6-diisopropylphenyl)acetamide as colorless needle-like crystals.

Potassium carbonate (76 mg, 0.55 mmols) was added to an acetone (2 ml) solution of the resulting anilide (149 mg, 0.5 mmols) and 2-mercaptobenzoxazole (83 mg, 0.55 mmols), and stirred at room temperature for 3 hours. The reaction mixture was diluted with an aqueous saturated solution of ammonium chloride, and extracted with ethyl acetate. The organic layer was washed with water, and dried with anhydrous magnesium sulfate, and the solvent was evaporated. Then, the residue was purified through silica gel column chromatogrpahy (developer: hexane/ether=3/1), and the resulting crystals were recrystallized from methylene chloride-ether-hexane. 156 mg (yield: 85%) of the intended product was obtained as colorless needle-like crystals.

m.p.: 156–158° C.

IR (KBr) cm$^{-1}$: 3272, 2963, 1665, 1135, 742

$^1$H-NMR (CDCl$_3$) δ: 1.07 (12H, br d, J=6.8 Hz), 3.01 (2H, sept, J=6.8 Hz), 4.11 (2H, s), 7.14 (1H, d, J=7.3 Hz), 7.23–7.34 (3H, m), 7.46–7.59 (2H, m)

EIMS m/z (relative intensity): 368 (M$^+$), 217 (100)

Elementary Analysis: for C$_{21}$H$_{24}$N$_2$O$_2$S Calculated: C, 68.45; H, 6.56; N, 7.60; S, 8.70 Measured: C, 68.59; H, 6.55; N, 7.60; S, 8.57

Example 2

Production of 3-(benzoxazol-2-ylthio)-N-(2,6-diisopropylphenyl)propanamide:

Ethanol (EtOH) (35 ml), 3-bromopropanoic acid (1.53 g, 10 mmols) and 2-mercaptobenzoxazole (1.51 g, 10 mmols) were added in that order to an aqueous (15 ml) solution of potassium hydroxide (KOH) (1.0 g, 17.8 mmols), and heated under reflux for 3 hours. The reaction mixture was concentrated under reduced pressure, water was added to the resulting residue, and this was made acidic (pH=1) with 1N HCl added thereto. The precipitate formed was taken out through filtration, and crystallized in acetone-ether-hexane to obtain 1.3 g (58% of 3-benzoxazol-2-ylthio)propanoic acid as colorless crystals.

WSC (211 mg, 1.1 mmols) and HOBt (148 mg, 1.1 mmols) were added in that order to an DMF (5 ml) solution of the carboxylic acid (223 mg, 1 mmol) prepared above and 2,6-diisopropylaniline (178 mg, 1 mmol), and stirred at room temperature for 12 hours. Water was added to the reaction mixture, which was then extracted with ethyl acetate. The organic layer was washed with 1 N HCl, an aqueous saturated solution of sodium hydrogencarbonate and saturated saline in that order, and dried with anhydrous sodium sulfate, and the solvent was evaporated. Then, the residue was purified through silica gel column chromatography (developer: hexane/acetone=5/1), and the resulting crystals were recrystallized from acetone-ether-hexane. 211 mg (yield: 55%) of the intended product was obtained as colorless needle-like crystals.

m.p.: 174–176° C.

IR (KBr) cm$^{-1}$: 3432, 3244, 1652, 1501, 1454

$^1$H-NMR (d$_6$-DMSO) δ: 1.14 (12H, d, J=6.8 Hz), 2.97 (2H, t, J=6.6 Hz), 3.13 (2H, sept, J=6.8 Hz), 3.64 (2H, t, J=6.6 Hz), 7.10–7.16 (2H, m), 7.23 (1H, dd, J=8.5, 6.8 Hz), 7.27–7.37 (2H, m), 7.56–7.64 (2H, m), 8.96 (1H, br s)

EIMS m/z (relative intensity): 382 (M$^+$), 232 (100)

Elementary Analysis: for C$_{22}$H$_{26}$N$_2$O$_2$S Calculated: C, 69.08; H, 6.85; N, 7.32 Measured: C, 69.24; H, 6.91; N, 7.29

[0045]

Example 3

Production of 4-(benzoxazol-2-ylthio)-N-(2,6-diisopropylphenyl)butanamide:

WSC (2.3 g, 12 mmols) and HOBt (1.49 g, 15 mmols) were added to a DMF (30 ml) solution of 2,6-diisoproylaniline (1.97 g, 10 mmols) and 4-bromobutyric acid (2.71 g, 15 mmols), and stirred at room temperature for 12 hours. The reaction mixture was extracted with ether. The organic layer was washed with water, 1 N HCl, an aqueous saturated solution of sodium hydrogencarbonate and saturated saline in that order, and dried with anhydrous magnesium sulfate, and the solvent was evaporated. Then, the residue was purified through silica gel column chromatography (developer: hexane/acetone=5/1), and the resulting crystals were recrystallized from ether-hexane to obtain 1.04 g (32%) of 4-bromo-N-(2,6-diisopropylphenyl)butanamide as colorless needle-like crystals.

Potassium carbonate (46 mg, 0.33 mmols) and 18-crown-6 (8 mg, 0.03 mmols) were added to a DMF (2 ml) solution of the resulting anilide (98 mg, 0.3 mmols) and 2-mercaptobenzoxazole (45 mg, 0.3 mmols), and stirred at 80° C. for 1 hour. The reaction mixture was diluted with water, and extracted with ether. The organic layer was washed with water, and dried with anhydrous magnesium sulfate, and the solvent was evaporated. Then, the residue was purified through preparative thin-layer chromatography (developer: hexane/acetone=5/1), and the resulting crystals were recrystallized from acetone-ether-hexane. 80 mg (67%) of the intended product was obtained as colorless needle-like crystals.

m.p.: 141–142° C.

IR (KBr) cm$^{-1}$: 3429, 3237, 1648, 1501, 1454

$^1$H-NMR (d$_6$-DMSO) δ: 1.22 (12H, d, J=6.8 Hz), 2.23–2.34 (2H, m), 2.61–2.72 (2H, m), 3.19 (2H, sept, J=6.8 Hz), 3.55 (2H, t, J=7.3 Hz), 7.21 (2H, m), 7.32 (1H, dd, J=8.5, 6.8 Hz), 7.39 (1H, ddd, J=8.0, 7.3, 1.5 Hz), 7.43 (1H, ddd, J=8.0, 7.3, 1.5 Hz), 7.64–7.73 (2H, m), 8.95 (1H, br s)

EIMS m/z (relative intensity): 396 (M$^+$, 100)

Elementary Analysis: for C$_{23}$H$_{28}$N$_2$O$_2$S Calculated: C, 69.66; H, 7.12; N, 7.06 Measured: C, 69.86; H, 7.32; N, 7.06

Example 4

Production of 5-(benzoxazol-2-ylthio)-N-(2,6-diisopropylphenyl)pentanamide:

WSC (2.87 g, 15 mmols) and HOBt (2.03 g, 15 mmols) were added to a DMF (20 ml) solution of 2,6- diisoproylaniline (1.97 g, 10 mmols) and 5-bromopentanoic acid (2.71 g, 15 mmols), and stirred at room temperature for 12 hours. The reaction mixture was extracted with ether. The organic layer was washed with water, 1 N HCl, an aqueous saturated solution of sodium hydrogencarbonate and saturated saline in that order, and dried with anhydrous magnesium sulfate, and the solvent was evaporated. Then, the residue was purified through silica gel column chromatography (developer: hexane/acetone=5/1), and the resulting crystals were recrystallized from ether-hexane to obtain 1.4 g (41%) of 5-bromo-N-(2,6-diisopropylphenyl)pentanamide as colorless needle-like crystals.

Potassium carbonate (46 mg, 0.33 mmols) and 18-crown-6 (8 mg, 0.03 mmols) were added to a DMF (2 ml) solution of the resulting anilide (102 mg, 0.3 mmols) and 2-mercaptobenzoxazole (45 mg, 0.3 mmols), and stirred at 80° C. for 1 hour. The reaction mixture was diluted with water, and extracted with ether. The organic layer was washed with water, and dried with anhydrous magnesium sulfate, and the solvent was evaporated. Then, the residue was purified through partitioning thin-layer chromatography (developer: chloroform/methanol=19/1), and the resulting crystals were recrystallized from acetone-ether-hexane. 86 mg (70%) of the intended product was obtained as colorless needle-like crystals.

m.p.: 122–123° C.

IR (KBr) cm$^{-1}$: 3424, 3252, 1651, 1501, 1454

$^1$H-NMR (d$_6$-DMSO) δ: 1.12 (12H, d, J=6.8 Hz), 1.79–2.01 (4H, m), 2.40–2.50 (2H, m), 3.09 (2H, sept, J=6.8 Hz), 3.41 (2H, t, J=6.8 Hz), 7.11 (2H, m), 7.22 (1H, dd, J=8.5, 6.8 Hz), 7.29 (1H, ddd, J=8.0, 7.3, 1.5 Hz), 7.33 (1H, ddd, J=8.0, 7.3, 1.5 Hz), 7.59 (2H, m), 8.76 (1H, br s)

EIMS m/z (relative intensity): 410 (M$^+$, 100)

Elementary Analysis: for C$_{24}$H$_{30}$N$_2$O$_2$S Calculated: C, 70.21; H, 7.36; N, 6.82 Measured: C, 70.06; H, 7.49; N, 6.90

Example 5

Production of 6-(benzoxazol-2-ylthio)-N-(2,6-diisopropylphenyl)hexanamide:

WSC (2.1 g, 11 mmols) and HOBt (1.49 g, 11 mmols) were added to a DMF (30 ml) solution of 2,6-diisoproylaniline (1.97 g, 10 mmols) and 6-bromopentanoic acid (2.93 g, 15 mmols), and stirred at room temperature for 15 hours. The reaction mixture was extracted with ether. The organic layer was washed with water, 1 N HCl, an aqueous saturated solution of sodium hydrogencarbonate and saturated saline in that order, and dried with anhydrous magnesium sulfate, and the solvent was evaporated. Then, the residue was purified through silica gel column chromatography (developer: hexane/acetone=5/1), and the resulting crystals were recrystallized from ether-hexane to obtain 2.15 g (61%) of 6-bromo-N-(2,6-diisopropylphenyl)hexanamide as colorless needle-like crystals.

Potassium carbonate (104 mg, 0.55 mmols) and 18-crown-6 (13 mg, 0.05 mmols) were added to a DMF (1 ml) solution of the resulting anilide (194 mg, 0.55 mmols) and 2-mercaptobenzoxazole (76 mg, 0.5 mmols), and stirred at 80° C. for 2 hours. The reaction mixture was diluted with an aqueous saturated solution of ammonium chloride, and extracted with ethyl acetate. The organic layer was washed with water, and dried with anhydrous magnesium sulfate, and the solvent was evaporated. Then, the residue was purified through silica gel column chromatography (developer: chloroform/methanol=20/1), and the resulting crystals were recrystallized from ether-hexane. 176 mg (yield 83%) of the intended product was obtained as colorless needle-like crystals.

m.p.: 116–118° C.

IR (KBr) cm$^{-1}$: 3431, 2965, 1645, 1454, 741

$^1$H-NMR (d$_6$-DMSO) δ: 1.12 (12H, d, J=6.8 Hz), 1.40–1.95 (6H, m), 2.39 (2H, m), 3.09 (2H, sept, J=6.8 Hz), 3.35 (2H, t, J=6.8 Hz), 7.21 (1H, d, J=8.3 Hz), 7.22 (1H, d, J=7.1 Hz), 7.33 (1H, dd, J=8.3, 7.1 Hz), 7.41 (1H, ddd, J=8.1, 7.1, 2.4 Hz), 7.44 (1H, ddd, J=8.1, 7.1, 2.4 Hz), 7.69 (1H, ddd, J=8.1, 2.4, 0.9 Hz), 7.71 (1H, ddd, J=7.1, 2.4, 0.9 Hz), 8.70 (1H, br s)

EIMS m/z (relative intensity): 424 (M$^+$, 100)

Elementary Analysis: for C$_{25}$H$_{32}$N$_2$O$_2$S Calculated: C, 70.72; H, 7.60; N, 6.60 Measured: C, 70.42; H, 7.71; N, 6.49

Example 6

Production of 7-(benzoxazol-2-ylthio)-N-(2,6-diisopropylphenyl)heptanamide:

2 N Jones' reagent (20 ml) was gradually and dropwise added to an acetone (20 ml) solution of 7-bromoheptanol (1.95 g, 10 mmols) with cooling with ice, and then stirred at room temperature for 10 minutes. The reaction mixture was extracted three times with ether (80 ml). The organic layer was washed with water, and then extracted three times with an aqueous saturated solution of sodium hydrogencarbonate (120 ml). The aqueous layers were combined, then made acidic (pH=1) with 5% sulfuric acid added thereto, and extracted with ethyl acetate. The resulting organic layer was washed with water and saturated saline in that order, and dried with anhydrous sodium sulfate, and the solvent was evaporated. 1.45 g (70%) of 7-bromoheptanoic acid was obtained as colorless needle-like crystals. WSC (891 g, 4.7 mmols) and HOBt (628 g, 4.7 mmols) were added to a DMF (20 ml) solution of the resulting carboxylic acid (1.06 g, 5 mmols) and 2,6-diisoproylaniline (738 g, 4.2 mmols), and stirred at room temperature for 12 hours. The reaction mixture was extracted with ether. The organic layer was washed with water, 1 N HCl, an aqueous saturated solution of sodium hydrogencarbonate and saturated saline in that order, and dried with anhydrous magnesium sulfate, and the solvent was evaporated. Then, the residue was purified through silica gel column chromatography (developer: hexane/acetone=5/1), and the resulting crystals were recrystallized from ether-hexane to obtain 466 g (yield: 30%) of 7-bromo-N-(2,6-diisopropylphenyl)heptanamide as colorless needle-like crystals.

Potassium carbonate (46 mg, 0.33 mmols) and 18-crown-6 (8 mg, 0.03 mmols) were added to a DMF (2 ml) solution of the resulting anilide (111 mg, 0.3 mmols) and 2-mercaptobenzoxazole (45 mg, 0.3 mmols), and stirred at 80° C. for 1 hour. The reaction mixture was diluted with water, and extracted with ether. The organic layer was washed with water, and dried with anhydrous magnesium sulfate, and the solvent was evaporated. Then, the residue was purified through preparative thin-layer chromatography (developer: chloroform/methanol=19/1), and the resulting crystals were recrystallized from acetone-ether-hexane. 104 mg (79%) of the intended product was obtained as colorless needle-like crystals.

m.p.: 127–128° C.

IR (KBr) cm$^{-1}$: 3425, 3249, 1648, 1562, 1454

$^1$H-NMR (d$_6$-DMSO) δ: 1.26 (12H, d, J=6.8 Hz), 1.56–2.05 (8H, m), 2.46–2.54 (2H, m), 3.23 (2H, sept, J=6.8 Hz), 3.49 (2H, t, J=7.3 Hz), 7.24 (2H, m), 7.34 (1H, dd, J=8.5, 6.8 Hz), 7.42 (1H, ddd, J=8.0, 7.3, 1.5 Hz), 7.46 (1H, ddd, J=8.0, 7.3, 1.5 Hz), 7.66–7.77 (2H, m), 8.82 (1H, br s)

EIMS m/z (relative intensity): 438 (M+, 100)

Elementary Analysis: for $C_{26}H_{34}N_2O_2S$ Calculated: C, 70.62; H, 7.84; N, 6.33 Measured: C, 70.70; H, 7.97; N, 6.24

Example 7

Production of 8-(benzoxazol-2-ylthio)-N-(2,6-diisopropylphenyl)octanamide:

WSC (1.05 g, 5.5 mmols) and HOBt (743 g, 5.5 mmols) were added to a DMF (15 ml) solution of 2,6-diisoproylaniline (886 g, 5 mmols) and 8-bromooctanoic acid (1.67 g, 7.5 mmols), and stirred at room temperature for 12 hours. The reaction mixture was extracted with ether. The organic layer was washed with water, 1 N HCl, an aqueous saturated solution of sodium hydrogencarbonate and saturated saline in that order, and dried with anhydrous magnesium sulfate, and the solvent was evaporated. Then, the residue was purified through silica gel column chromatography (developer: hexane/acetone=5/1), and the resulting crystals were recrystallized from ether-hexane to obtain 720 mg (yield: 38%) of 8-bromo-N-(2,6-diisopropylphenyl)octanamide as colorless needle-like crystals.

Potassium carbonate (46 mg, 0.33 mmols) and 18-crown-6 (8 mg, 0.03 mmols) were added to a DMF (2 ml) solution of the resulting anilide (115 mg, 0.3 mmols) and 2-mercaptobenzoxazole (45 mg, 0.3 mmols), and stirred at 80° C. for 1 hour. The reaction mixture was diluted with water, and extracted with ether. The organic layer was washed with water, and dried with anhydrous magnesium sulfate, and the solvent was evaporated. Then, the residue was purified through preparative thin-layer chromatography (developer: chloroform/methanol=19/1), and the resulting crystals were recrystallized from acetone-ether-hexane. 102 mg (75%) of the intended product was obtained as colorless needle-like crystals.

m.p.: 126–127° C.

IR (KBr) cm$^{-1}$: 3433, 3263, 1652, 1505, 1454

$^1$H-NMR (d$_6$-DMSO) δ: 1.27 (12H, d, J=6.8 Hz), 1.51–2.02 (10H, m), 2.45–2.52 (2H, m), 3.24 (2H, sept, J=6.8 Hz), 3.50 (2H, t, J=7.3 Hz), 7.25 (2H, m), 7.35 (1H, dd, J=8.5, 6.8 Hz), 7.43 (1H, ddd, J=8.0, 7.3, 1.5 Hz), 7.46 (1H, ddd, J=8.0, 7.3, 1.5 Hz), 7.73 (2H, m), 8.81 (1H, br s)

EIMS m/z (relative intensity): 452 (M+, 100)

Elementary Analysis: for $C_{27}H_{36}N_2O_2S$ Calculated: C 71.64; H8.02; N 6.19 Measured: C 71.65; H 8.15; N 6.35

Example 8

Production of 9-(benzoxazol-2-ylthio)-N-(2,6-diisopropylphenyl)nonanamide:

2N Jones' reagent (20 ml) was gradually and dropwise added to an acetone (20 ml) solution of 9-bromononanol (2.2 g, 10 mmols) with cooling with ice, and then stirred at room temperature for 10 minutes. The reaction mixture was extracted three times with hexane (40 ml). The organic layer was washed with water, and then extracted three times with an aqueous saturated solution of potassium carbonate (40 ml). The aqueous layers were combined, then made acidic (pH=1) with 10% sulfuric acid added thereto, and extracted with ethyl acetate. The resulting organic layer was washed with water and saturated saline in that order, and dried with anhydrous sodium sulfate, and the solvent was evaporated. 1.8 g (yield: 77%) of 9-bromononanoic acid was obtained as colorless needle-like crystals.

WSC (880 mg, 4.6 mmols) and HOBt (621 mg, 4.6 mmols) were added to a DMF (20 ml) solution of the resulting carboxylic acid (1.19 g, 5 mmols) and 2,6-diisopropylaniline (738 mg, 4.2 mmols), and stirred at room temperature for 12 hours. The reaction mixture was extracted with ether. The organic layer was washed with water, 1N HCl, an aqueous saturated solution of sodium hydrogencarbonate and saturated saline in that order, and dried with anhydrous magnesium sulfate, and the solvent was evaporated. Then, the residue was purified through silica gel column chromatography (developer: hexane/acetone=5/1), and the resulting crystals were recrystallized from ether-hexane to obtain 666 mg (yield 34%) of 9-bromo-N-(2,6-diisoopropylphenyl)nonanamide as colorless needle-like crystals.

Potassium carbonate (46 mg, 0.33 mmols) and 18-crown-6 (8 mg, 0.03 mmols) were added to a DMF (2 ml) solution of the resulting anilide (119 mg, 0.3 mmols) and 2-mercaptobenzoxazole (45 mg, 0.3 mmols), and stirred at 80° C. for 1 hour. The reaction mixture was diluted with water, and extracted with ether. The organic layer was washed with water, and dried with anhydrous magnesium sulfate, and the solvent was evaporated. Then, the residue was purified through preparative thin-layer chromatography (developer: hexane/acetone=5/1), and the resulting crystals were recrystallized from acetone-ether-hexane. 98 mg (yield: 70%) of the intended product was obtained as colorless needle-like crystals.

m.p.: 76–77° C.

IR (KBr) cm$^{-1}$: 3424, 3253, 1650, 1504, 1455

$^1$H-NMR (d$_6$-DMSO) δ: 1.28 (12H, d, J=6.8 Hz), 1.46–2.05 (12H, m), 2.44–2.56 (2H, m), 3.25 (2H, sept, J=6.8 Hz), 3.50 (2H, t, J=7.3 Hz), 7.26 (2H, m), 7.37 (1H, dd, J=8.5, 6.8 Hz), 7.43 (1H, ddd, J=8.0, 7.3, 1.5 Hz), 7.47 (1H, ddd, J=8.0, 7.3, 1.5 Hz), 7.66–7.77 (2H, m), 8.82 (1H, br s)

EIMS m/z (relative intensity): 466 (M+, 100)

Elementary Analysis: for $C_{28}H_{38}N_2O_2S$ Calculated: C 72.06; H 8.21; N 6.00 Measured: C 72.15; H 8.39; N 5.91

Example 9

Production of 10-(benzoxazol-2-ylthio)-N-(2,6-diisopropylphenyl)decanamide:

2 N Jones' reagent (26 ml) was gradually and dropwise added to an acetone (26 ml) solution of 10-bromodecanol (3.0 g, 12.7 mmols) with cooling with ice, and then stirred at room temperature for 10 minutes. The reaction mixture was extracted three times with hexane (75 ml). The organic layer was washed with water, and then extracted three times with an aqueous saturated solution of potassium carbonate (75 ml). The aqueous layers were combined, then made acidic (pH=1) with 10% sulfuric acid added thereto, and extracted with ethyl acetate. The resulting organic layer was washed with water and saturated saline in that order, and dried with anhydrous sodium sulfate, an the solvent was evaporated. 2.5 g (yield: 78%) of 10-bromooctanoic acid was obtained as colorless needle-like crystals.

WSC (1.07 g, 5.6 mols) and HOBt (755 mg, 5.6 mmols) were added to a DMF (20 ml) solution of the resulting carboxylic acid (1.27 g, 5 mmols) and 2,6-diisopropylaniline (1.38 g, 7.6 mmols), and stirred at room temperature for 12 hours. The reaction mixture was extracted with ether. The organic layer was washed with water, 1 N HCl, an aqueous saturated solution of sodium hydrogencarbonate and saturated saline in that order, and dried with anhydrous magnesium sulfate, and the solvent was evaporated. Then, the residue was purified through silica gel column chromatography (developer: hexane/acetone=5/1), and the resulting crystals were recrystallized from ether-hexane to obtain 797 mg (yield: 38%) of 10bromo-N-(2,6-diisopropylphenyl) decanamide as colorless needle-like crystals.

Potassium carbonate (46 mg, 0.33 mmols) and 18-crown-6 (8 mg, 0.03 mmols) were added to a DMF (2 ml) solution of the resulting anilide (123 mg, 0.3 mmols) and 2-mercaptobenzoxazole (45 mg, 0.3 mmols), and stirred at 80° C. for 1 hour. The reaction mixture was diluted with water, and extracted with ether. The organic layer was washed with water, and dried with anhydrous magnesium sulfate, and the solvent was evaporated. Then, the residue was purified through partitioning thin-layer chromatography (developer: hexane/acetone=5/1), and the resulting crystals were recrystallized from acetone-ether-hexane. 84 mg (58%) of the intended product was obtained as colorless needle-like crystals.

m.p.: 61–63° C.

IR (KBr) cm$^{-1}$: 3441, 3241, 1647, 1501, 1455

$^1$H-NMR (d$_6$-DMSO) δ: 1.28 (12H, d, J=6.8Hz), 1.46–2.02 (14H, m), 2.44–2.56 (2H, m), 3.24 (2H, sept, J=6.8Hz), 3.50 (2H, t, J=7.3 Hz), 7.26 (2H, m), 7.37 (1H, dd, J=8.5, 6.8 Hz), 7.44 (1H, ddd, J=8.0, 7.3, 1.5 Hz), 7.47 (1H, ddd, J=8.0, 7.3, 1.5 Hz), 7.69–7.79 (2H, m), 8.93 (1H, br s)

EIMS m/z (relative intensity): 480 (M$^+$, 100)

Elementary Analysis: for C$_{29}$H$_{40}$N$_2$O$_2$S Calculated: C 72.46; H 8.39; N 5.83 Meassured: C 72.24; J 8.65; N 5.82

Example 10

Production of 15-(benzoxazol-2-ylthio)-N-(2,6-diisopropylphenyl)pentadecanamide:

15-pentadecanolactone (10 g, 42 mmols), potassium hydroxide (10 g, 0.18 mmols) and tetra-n-butylammonium bromide (1.34 g, 4.2 mmols) were dissolved in a mixed solvent of THF (100 ml) and water (30 ml), and heated under reflux for 12 hours. The reaction mixture was concentrated under reduced pressure to evaporate THF, and the aqueous layer was made acidic (pH=1) and then extracted with ether. The organic layer was washed with water and saturated saline in that order, and dried with anhydrous sodium sulfate, and the solvent was evaporated. The residue was recrystallized from acetone to obtain 10.4 g (yield: 97%) of 15-hydroxypentadecanoic acid as colorless needle-like crystals.

WSC (4.2 g, 22 mmols) and HOBt (3.0 g, 22 mmols) were added to a DMF (40 ml) solution of the resulting carboxylic acid (5.2 g, 20 mmols) and 2,6-diisopropylaniline (5.3 g, 30 mmols), and stirred at room temperature for 12 hours. Water was added to the reaction mixture, and the precipitate formed was taken out through filtration, and extracted with chloroform. The organic layer was washed with 1 N HCl and saturated saline in that order, and dried with anhydrous sodium sulfate, and the solvent was evaporated. The residue was extracted with ether and filtered, and the filtrate was concentrated under reduced pressure. The residue was purified through silica gel column chromatography (developer: hexane/acetone=5/1) to obtain 1.9 g (yield: 23%) of N-(2, 6-diisopropylphenyl)-15-hydroxypentadecanamide.

To a pyridine solution (15 ml) of the thus-obtained anilide (1.64 g, 3.9 mmols), added were p-toluenesulfonyl chloride (TsCl) (1.65 g, 8.7 mmols) and N,N-dimethyl-4-aminopyridine (24 mg, 0.2 mmols), and stirred at room temperature for 12 hours. Water was added to the reaction mixture, which was then extracted with ether. The organic layer was washed with an aqueous solution of 5% potassium hydrogensulfate, saturated saline, an aqueous saturated solution of sodium hydrogencarbonate and saturated saline in that order, and dried with anhydrous sodium sulfate, and the solvent was evaporated. The residue was purified through silica gel column chromatography (developer: hexane/ ether=3/1) to obtain 622 mg (yield: 29%) of N-(2,6-diisoopropylphenyl)-15-(4-toluenesulfonyloxy) pentadecanamide and 177 mg (yield: 10%) of N-(2,6-diisopropylphenyl)-15-chloropentadecanamide.

Potassium carbonate (55mg, 0.4 mmols) and 18-crown-6 (10 mg, 0.04 mmols) were added to a DMF (2 ml) solution of the resulting chloride (164 mg, 0.38 mmols) and 2-mercaptobenzoxazole (55 mg, 0.36 mmols), and stirred at 80° C. for 1 hour. The reaction mixture was diluted with water, and extracted with ether. The organic layer was washed with water, and dried with anhydrous sodium sulfate, and the solvent was evaporated. Then, the residue was purified through silica gel column chromatography (developer: hexane/acetone=15/1), and the resulting crystals were recrystallized from ether-hexane. 165 mg (yield: 83%) of the intended product was obtained as colorless needle-like crystals.

m.p.: 64–65° C.

IR (KBr) cm$^{-1}$: 3429, 3248, 1649, 1503, 1455

$^1$H-NMR (d$_6$-DMSO) δ: 1.13 (12H, d, J=6.8 Hz), 1.25–1.72 ) (22H, m), 1.81 (2H, quint, J=7.3 Hz), 2.29–2.38 (2H, m), 3.10 (2H, sept, J=6.8 Hz), 3.33 (2H, t, J=7.3 Hz), 7.08–7.14 (2H, m), 7.21 (1H, dd, J=8.5, 6.8 Hz), 7.2–7.35 (2H, m), 7.53–7.63 (2H, m), 8.67 (1H, br s)

EIMS m/z (relative intensity): 550 (M$^+$, 100)

Elementary Analysis: for C$_{34}$H$_{50}$N$_2$O$_2$S Calculated: C 7414; H 9.15; N 5.09 Measured: C 74.10; H 9.25; N 5.09

Example 11 production of 2-(benzoxazol-2-ylthio)-N-(2,4-difluorophenyl)acetamide:

WSC (2.1 g, 11 mmols) and HOBt (1.49 g, 11 mmols) were added to a DMF (30 ml) solution of 2,4-difluroaniline (1.29g, 10 mmols) an bromoacetic acid (2.08 g, 15 mmols), and stirred at room temperature for 12 hours. The reaction mixture was extracted with ether. The organic layer was washed with water, 1 N HCl, an aqueous saturated solution of sodium hydrogencarbonate and saturated saline in that order, and dried with anhydrous magnesium sulfate, and the solvent was evaporated. Then, the residue was purified through silica gel column chromatography (developer: hexane/acetone=5/1), and the resulting crystals were recrystallized from ether-hexane to obtain 1.7 g (yield: 68%) of 2-bromo-N-(2,4-difluorophenyl)acetamide as colorless needle-like crystals.

Potassium carbonate (46 mg, 0.33 mmols) was added to an acetone (2 ml) solution of the resulting anilide (75 mg, 0.3 mmols) and 2-mercaptobenzoxazole (45 mg, 0.3 mmols), and stirred at room temperature for 1 hour. The reaction mixture was diluted with water, and extracted with ether. The organic layer was washed with water, and dried with anhydrous magnesium sulfate, and the solvent was evaporated. Then, the residue was purified through partitioning thin-layer chromatography (developer: hexane/ acetone=5/1), and the resulting crystals were recrystallized from methylene chloride-ether-hexane. 80 mg (yield: 83%) of the intended product was obtained as colorless needle-like crystals.

m.p.: 123–124° C.

IR (KBr) cm$^{-1}$; 3276, 1683, 1558, 1500, 1139

$^1$H-NMR (CDCl$_3$) δ: 4.03 (2H, s), 6.76–6.89 (3H, m) 7.30 (1H, dt, J=7.3, 1.5 Hz), 7.36 (1H, dt, J=7.3, 1.5 Hz), 7.49 (1H, ddd, J=7.3, 1.5, 0.5 Hz), 8.34 (1H, m), 10.21 (2H, br s)

EIMS m/z (relative intensity): 320 (M$^+$), 161 (100)

Elementary Analysis: for C$_{15}$H$_{10}$F$_2$N$_2$O$_2$S Calculated: C 56.25; H 3.15; N 8.75 Measured: C 56.34; H 3.17; N 8.65

Example 12

Production of 4-(benzoxazol-2-ythio)-N-(2,4-diflurorphenyl)butanamide:

WSC (2.1 g, 11 mmols) and HOBt (1.49 g, 11 mmols) were added to a DMF (30 ml) solution of 2,4-difluoroaniline (1.29 g, 10 mmols) and 4-bromobutyric acid (2.5 g, 15 mols), and stirred at room temperature for 12 hours. The reaction mixture was extracted with ether. The organic layer was washed with water, 1 N HCl, an aqueous saturated solution of sodium hydrogencarbonate and saturated saline in that order, and dried with anhydrous magnesium sulfate, and the solvent was evaporated. Then, the residue was purified through preparative thin-layer chromatography (developer: hexane/acetone=5/1), and the resulting crystals were recrystallized from ether-hexane to obtain 1.6 g (yield: 58%) of 4-bromo-N-(2,4-difluorophenyl)butanamide as colorless needle-like crystals.

Potassium carbonate (46 mg, 0.33 mmols) and 18-crown-6 (8 mg, 0.03 mmols) were added to a DMF (2 ml) solution of the resulting anilide (83 mg, 0.3 mmols) and 2-mercaptobenzoxazole (45 mg, 0.3 mmols), and stirred at 80° C. for 2 hours. The reaction mixture was diluted with water, and extracted with ether. The organic layer was washed with water, and dried with anhydrous magnesium sulfate, and the solvent was evaporated. Then, the residue was purified through preparative thin-layer chromatography (developer: hexane/acetone=5/1), and the resulting crystals were recrystallized from acetone-ether-hexane. 60 mg (yield: 57%) of the intended product was obtained as colorless needle-like crystals.

m.p.: 95–96° C.

IR (KBr) cm$^{-1}$: 3292, 1668, 1545, 1501, 1455

$^1$H-NMR (CDCl$_3$) δ: 2.31 (2H, quint, J=6.8 Hz), 2.64 (2H, t, J=6.8 Hz), 3.44 (2H, t, J=6.8 Hz), 6.82–6.92 (2H, m), 7.20–7.31 (2H, m), 7.42 (1H, m), 7.52 (1H, m), 7.85 (1H, br s), 8.20 (1H, m)

EIMS m/z (relative intensity): 348 (M$^+$), 219 (100)

Elementary Analysis: for C$_{17}$H$_{14}$F$_2$N$_2$O$_2$S Calculated: C 58.61; H 4.05; N 8.04 Measured: C 58.64; H 4.06; N 8.00

Example 13

Production of 5-(benzoxazol-2-ylthio)-N-(2,4-difluorophenyl)pentanamide:

WSC (2.1 g, 11 mmols), and HOBt (1.49 g, 11 mmols) were added to a DMF (30 ml) solution of 2,4-difluoroaniline (1.29 g, 10 mmols) and 5-bromopentanoic acid (2.7 g, 15 mmols), and stirred at room temperature for 12 hours. The reaction mixture was extracted with ether. The organic layer was washed with water, 1 N HCl, an aqueous saturated solution of sodium hydrogencarbonate and saturated saline in that order, and dried with anhydrous magnesium sulfate, and the solvent was evaporated. Then, the residue was purified through preprative thin-layer chromatography (developer: hexane/acetone=5/1), and the resulting crystals were recrystallized from ether-hexane to obtain 2.0 g (yield: 68%) of 5-bromo-N-(2,4-difluorophenyl)pentanamide as colorless needle-like crystals.

Potassium carbonate (46 mg, 0.33 mmols) and 18-crown-6 (8 mg, 0.03 mmols) were added to a DMF (2 ml) solution of the resulting anilide (88 mg, 0.3 mmols) and 2-mercaptobenzoxazole (45 mg, 0.3 mmols), and stirred at 80° C. for 1 hour. The reaction mixture was diluted with water, and extracted with ether. The organic layer was washed with water, and dried with anhydrous magnesium sulfate, and the solvent was evaporated. Then, the residue was purified through partitioning thin-layer chromatography (developer: hexane/acetone=5/3), and the resulting crystals were recrystallized from acetone-ether-hexane. 75 mg (yield: 69%) of the intended product was obtained as colorless needle-like crystals.

m.p.: 136–137° C.

IR (KBr) cm$^{-1}$: 3439, 3248, 1663, 1533, 1504

$^1$H-NMR (CDCl$_3$) δ: 1.90–1.97 (4H, m), 2.45–2.51 (2H, m), 3.33–3.39 (2H, m), 6.80–6.90 (2H, m), 7.20–7.31 (3H, m), 7.43 (1H, m), 7.58 (1H, m), 8.20 (1H, m)

EIMS m/z (relative intensity): 362 (M$^+$), 233 (100)

Elementary Analysis: for C$_{18}$H$_{16}$F$_2$N$_2$O$_2$S.0.25H$_2$O Calculated: C 58.92; H 4.53; N 7.64 MEasured: C 58.94; H 4.42; N 7.59

Example 14

Production of 6-(benzoxazol-2-ylthio)-N-(2,4-difluorophenyl)hexanamide:

WSC (2.1 g, 11 mmols) and HOBt (1.49 g, 11 mmols) were added to a DMF (30 ml) solution of 2,4-difluoroaniline (1.29 g, 10 mmols) and 6-bromohexanoic acid (2.93 g, 15 mmols), and stirred at room temperature for 15 hours. The reaction mixture was extracted with ether. The organic layer was washed with water, 1 N HCl, an aqueous saturated solution of sodium hydrogencarbonate and saturated saline in that order, and dried with anhydrous magnesium sulfate, and the solvent was evaporated. Then, the residue was purified through silica gel column chromatography (developer: hexane/acetone=5/1), and the resulting crystals were recrystallized from ether-hexane to obtain 2.1 g (yield: 69%) of 6-bromo-N-(2,4-difluorophenyl)hexanamide as colorless needle-like crystals.

Potassium carbonate (30 mg, 0.22 mmols) and 18-crown-6 (5 mg, 0.02 mmols) were added to a DMF (1 ml) solution of the resulting anilide (61 mg, 0.2 mmols) and 2-mercaptobenzoxazole (30 mg, 0.2 mmols), and stirred at 80° C. for 2 hours. The reaction mixture was diluted with water, and extracted with ether. The organic layer was washed with water, and dried with anhydrous magnesium sulfate, and the solvent was evaporated. Then, the residue was purified through partitioning thin-layer chromatography (developer: hexane/acetone=5/1), and the resulting crystals were recrystallized from ether-hexane. 63 mg (83%) of the intended product was obtained as colorless needle-like crystals.

m.p.: 104–105° C.

IR (KBr) cm$^{-1}$: 3293, 1659, 1537, 1507, 1132

$^1$H-NMR (d$_6$-DMSO) δ: 1.53–1.66 (2H, m), 1.75–1.95 (4H, m), 2.43 (2H, t, J=7.3 Hz), 3.32 (2H, t, J=7.3 Hz), 6.80–6.90 (2H, m), 7.19–7.31 (2H, m), 7.43 (1H, m), 7.59 (1H, m), 8.24 (1H, m)

EIMS m/z (relative intensity): 376 (M$^+$, 100)

Elementary Analysis: for C$_{19}$H$_{18}$F$_2$N$_2$O$_2$S Calculated: C 60.63; H 4.82; N 7.44 Measured: C 60.46; H 4.88; N 7.43

Example 15

Production of 10-(benzoxazol-2-ylthio)-N-(2,4-difluorophenyl)decanamide:

WSC (990 mg, 5.2 mmols) and HOBt (698 mg, 5.2 mmols) were added to a DMF (10 ml) solution of 2,4-difluoroaniline (1.29 g, 10 mmols) and 10-bromodecanoic acid (1.18 g, 4.7 mmols), and stirred at room temperature for 15 hours. The reaction mixture was extracted with ether. The organic layer was washed with water, 1 N HCl, an aqueous saturated solution of sodium hydrogencarbonate and saturated saline in that order, and dried with anhydrous magnesium sulfate, and the solvent was evaporated. Then, the residue was purified through silica gel column chromatography (developer: hexane/acetone=10/1), and the resulting crystals were recrystallized from ether-hexane to obtain 763 mg (yield: 45%) of 10-bromo-N-(2,4-difluorophenyl)decanamide as colorless needle-like crystals.

Potassium carbonate (46 mg, 0.33 mmols) and 18-crown-6 (8 mg, 0.03 mmols) were added to a DMF (2 ml) solution of the resulting anilide (109 mg, 0.3 mmols) and 2-mercaptobenzoxazole (45 mg, 0.3 mmols), and stirred at 80° C. for 1 hour. The reaction mixture was diluted with water, and extracted with ether. The organic layer was washed with water, and dried with anhydrous sodium sulfate, and the solvent was evaporated. Then, the residue was purified through preparative thin-layer chromatography (developer: hexane/acetone=5/1), and the resulting crystals were recrystallized from ether-hexane. 80 mg (yield: 61%) of the intended product was obtained as colorless needle-like crystals.

m.p.: 102–103° C.

IR (KBr) cm$^{-1}$: 3436, 3296, 1658, 1534, 1507

$^1$H-NMR (CDCl$_3$) δ: 1.25–1.55 (10H, m), 1.64–1.87 (4H, m), 2.39 (2H, t, J=7.3 Hz), 3.31 (2H, t, J=7.3 Hz), 6.81–6.91 (2H, m), 7.17–7.32 (3H, m), 7.43 (1H, m), 7.60 (1H, m), 8.26 (1H, m)

EIMS m/z (relative intensity): 432 (M$^+$, 100)

Elementary Analysis: for C$_{23}$H$_{26}$F$_2$N$_2$O$_2$S Calculated: C 63.87; H 6.06; N 6.48 Measured: C 63.94; H 6.11; N 6.48

Example 16

Production of 5-(benzoxazol-2-ylthio)-N-(2,6-diisopropylphenyl)-2,2-dimethylpentanamide:

Iodotrimethylsilane (3.00 g, 15 mmols) was added to an acetonitrile solution (5 ml) of ethyl 5-chloro-2,2-dimethylpentanoate (963 mg, 5 mmols) at room temperature, and heated at 80° C. for 24 hours with stirring. The reaction mixture was poured into water with ice, and extracted with ether. The organic layer was washed with water, and dried with anhydrous magnesium sulfate, and the solvent was evaporated to obtain 0.9 g of 5-chloro-2,2-dimethylpentanoic acid as a brown oil.

Oxalyl chloride (888 mg, 7 mmols) was added to a chloroform (10 ml) solution of the resulting carboxylic acid (0.9 g, 5 mmols) and DMF (catalytic amount, 1 drop), and stirred at room temperature for 1 hour. The reaction mixture was concentrated to obtain 5-chloro-2,2-dimethylpentanoic acid chloride.

A chloroform (2 ml) solution of the carboxylic acid chloride obtained in the above was added to a chloroform (3 ml) solution of 2,6-diisopropylaniline (532 mg, 3 mmols) and triethylamine (506 mg, 5 mmols) with cooling with ice, and then stirred at room temperature for 12 hours. The reaction mixture was diluted with water, and extracted with ether. The organic layer was washed with 1 N HCl, an aqueous saturated solution of sodium hydrogencarbonate and saturated saline in that order, and dried with anhydrous magnesium sulfate, and the solvent was evaporated.

The resulting residue was recrystallized from ether-hexane to obtain 833 mg (yield: 86%) of 5-chloro-2,2-dimethyl-N-(2,6-diisopropylphenyl)pentanamide as colorless needle-like crystals (m.p.: 172–174° C.).

Potassium carbonate (62 mg, 0.45 mmols) and 18-crown-6 (8 mg, 0.03 mmols) were added to a DMF (1.5 ml) solution of the resulting anilide (97 mg, 0.3 mmols) and 2-mercaptobenzoxazole (53 mg, 0.35 mmols), and stirred at 80° C. for 3 hours. The reaction mixture was diluted with water, and extracted with ethyl acetate. The organic layer was washed with water, and dried with anhydrous magnesium sulfate, and the solvent was evaporated. Then, the residue was purified through silica gel column chromatography (developer: hexane/acetone=7/1), and the resulting crystals (110 mg, yield: 84%) were recrystallized from actone-hexane. Thus was obtained the intended product as colorless needle-like crystals.

m.p.: 149–151° C.

IR (KBr) cm$^{-1}$: 3303, 2963, 1641, 1502, 1129

$^1$H-NMR (d$_6$-DMSO) δ: 1.11 (12H, d, J=6.8 Hz), 1.30 (6H, s), 1.77–1.98 (4H, m), 3.07 (2H, sept, J=6.8 Hz), 3.39 (2H, t, J=7.1 Hz), 7.10 (1H, d, J=8.3 Hz), 7.11 (2H, d, J=7.1 Hz), 7.21 (2H, dd, J=8.3, 7.1 Hz), 7.26–7.37 (2H, m), 7.53–7.64 (2H, m), 8.43 (1H, br s)

EIMS m/z (relative intensity): 438 (M$^+$, 100)

Elementary Analysis: for C$_{26}$H$_{34}$N$_2$O$_2$S Calculated: C 71.20; H 7.81; N 6.39; S 7.31 Measured: C 71.10; H 7.81; N 6.45; S 7.40

Example 17

Production of 6-(benzoxazol-2-ylthio)-2,2-tetramethylene-N-(2,6-diisopropylphenyl)hexanamide:

Methyl cyclopentanecarboxylate (1.3 g, 10 mmols) was gradually added to a tetrahyrofuran (THF) (10 ml) solution of lithium diisopropylamide (LDA) (11 mmols) at −78° C., and stirred for 30 minutes at said temperature. Then, still at said temperature, hexamethylphosphoramide (HMPA) (2.15 g, 12 mmols) and 1-bromo-4-chlorobutane (2.06 g, 12 mmols) were gradually added thereto in that order, and stirred for 2 hours still at −78° C. An aqueous saturated solution of ammonium chloride was added to the reaction mixture, which was then extracted with ether. The organic layer was washed with water and saturated saline in that order, and dried with anhydrous magnesium sulfate, and the solvent was evaporated. The residue was purified through silica gel column chromatography (developer: hexane/ether=10.1) to obtain 2.18 g (yield: 99%) of methyl 6-chloro-2,2-tetramethylene-hexanoate as a colorless oil.

A methylene chloride (1.0 mol/liter) solution (4 ml) of boron trichloride was gradually added to a methylene chloride (1 ml) solution of the resulting ester (219 mg, 1 mmol) at −20° C., and then stirred at room temperature for 2 hours. The reaction mixture was poured into water with ice, and extracted with methylene chloride. The organic layer was washed with water, and dried with anhydrous magnesium sulfate, and the solvent was evaporated to obtain 216 mg (yield: >99%) of 6-chloro-2,2-tetramethylenehexanoic acid as a colorless oil.

DMF (catalytic amount, 1 drop) and oxalyl chloride (152 mg, 1.2 mmols) were added in that order to a chloroform (3 ml) solution of the resulting carboxylic acid (164 mg, 0.8 mmols) with cooling with ice, and then stirred at room temperature for 30 minutes. The reaction mixture was concentrated to obtain the corresponding acid chloride.

A chloroform (1.5 ml) solution of the acid chloride prepared in the above was added to a chloroform (3 ml) solution of 2,6-diisopropylaniline (142 mg, 0.8 mmols) and triethylamine (81 mg, 0.8 mmols) with cooling with ice, and stirred at room temperature for 12 hours. The reaction mixture was diluted with water and extracted with ether. The organic layer was washed with 1 N HCl, an aqueous saturated solution of sodium hydrogencarbonate and saturated saline in that order, and dried with anhydrous magnesium sulfate, and the solvent was evaporated. The residue was recrystallized from ether-hexane to obtain 148 mg (yield: 58%) of 6-chloro-2,2-tetramethylene-N-(2,6-diisopropylphenyl)hexanamide as colorless needle-like crystals.

Potassium carbonate (30 mg, 0.22 mmols) and 18-crown-6 (5 mg, 0.02 mmols) were added to a DMF (1 ml) solution of the resulting anilide (63 mg, 0.2 mmols) and 2-mercaptobenzoxazole (30 mg, 0.2 mmols), and stirred at 80° C. for 1 hour. The reaction mixture was diluted with water, and extracted with ether. The organic layer was washed with water, and dried with anhydrous magnesium sulfate, and the solvent was evaporated. Then, the residue was purified through preparative thin-layer chromatography (developer: hexane/acetone=5/1), and the resulting crystals were recrystallized from acetone-ether-hexane. 46 mg (yield: 53%) of the intended product was obtained as colorless needle-like crystals.

m.p.: 115–117° C.

IR (KBr) cm$^{-1}$: 3431, 3308, 1642, 1506, 1454

$^1$H-NMR (CDCl$_3$) δ: 1.20 (12H, d, J=6.8 Hz), 1.52–1.94 (12H, m), 2.14–2.26 (2H, m), 3.04 (2H, sept, J=6.8 Hz), 3.32 (2H, t, J=7.3 Hz), 6.76 (1H, br s), 7.16 (2H, m), 7.19–7.32 (3H, m), 7.41–7.45 (1H, m), 7.56–7.61 (1H, m)

EIMS m/z (relative intensity): 478 (M$^+$, 100)

Elementary Analysis: for C$_{29}$H$_{38}$N$_2$O$_2$S Calculated: C 72.76; H 8.00; N 5.85 Measured: C 72.86; H 8.27; N 5.74

Example 18

Production of 6-(benzoxazol-2-ylthio)-2,2-trimethylene-N-(2,6-diisopropylphenyl)hexanamide:

Cyclobutanecarbonyl chloride (2.37 g, 20 mmols) was added to a chloroform (30 ml) solution of benzyl alcohol (2.16 g, 20 mmols) and triethylamine (2.2 g, 22 mmols) with cooling with ice, and then heated under reflux for 1 hour. The reaction mixture was concentrated under reduced pressure, and the residue was diluted with water and extracted with ether. The organic layer was washed with 1 N HCl, an aqueous saturated solution of sodium hydrogencarbonate and saturated saline in that order, and dried with anhydrous magnesium sulfate and the solvent was evaporated. The resulting oil was purified through silica gel column chromatography (developer: hexane/acetone=10/1) and distilled (110° C./1.2 mmHg) to obtain 2.14 g (yield: 56%) of benzyl cyclobutanecarboxylate as a colorless oil.

The resulting ester (951 mg, 5 mmols) was gradually added to a THF (10 ml) solution of LDA (5.5 mols) at −52° C., and stirred for 30 minutes at said temperature. Then, still at said temperature, HMPA (896 mg, 5 mmols) and 1-bromo-4-chlorobutane (857 mg, 5 mmols) were gradually added thereto in that order, and stirred for 1 hour still at −52° C. and then for 1 hour at −20° C. An aqueous saturated solution of ammonium chloride was added to the reaction mixture, which was then extracted with ether. The organic layer was washed with 1N HCl, an aqueous saturated solution of sodium hydrogencarbonate and saturated saline in that order, and dried with anhydrous magnesium sulfate, and the solvent was evaporated. The residue was distilled (190° C./2.0 mmHg) to obtain 526 mg (yield: 37%) of benzyl 6-chloro-2,2-trimethylenehexanoate as a colorless oil.

10% palladium-carbon catalyst (30 mg) was added to an ethyl acetate (5 ml) solution of the resulting ester (281 mg, 1 mmol), and stirred in a hydrogen atmosphere at room temperature for 2 hours. The reaction mixture was filtered, and the solvent was evaporated. The resulting residue was diluted with ether, and extracted with an aqueous saturated solution of sodium hydrogencarbonate. The aqueous layer was made acidic with 1N HCl added thereto, and then extracted with ethyl acetate. The resulting extract was washed with saturated saline, and dried with anhydrous magnesium sulfate, and the solvent was evaporated to obtain 120 mg (yield: 63%) of 6-chloro-2,2-trimethylenehexanoic acid as a colorless oil.

DMF (catalytic amount, 1 drop) and oxalyl chloride (116 mg, 0.91 mmols) were added in that order to a chloroform (2 ml) solution of the resulting carboxylic acid (116 mg, 0.61 mmols) with cooling with ice, and then stirred at room temperature for 30 minutes. The reaction mixture was concentrated to obtain 6-chloro-2,2-trimethylenehexanoic acid chloride.

A chloroform (1 ml) solution of the acid chloride prepared in the above was added to a chloroform (2 ml) solution of 2,6-diisopropylaniline (108 mg, 0.61 mmols) and triethylamine (82 mg, 0.61 mmols) with cooling with ice, and stirred at room temperature for 2 days. The reaction mixture was diluted with water and extracted with ether. The organic layer was washed with 1N HCl, an aqueous saturated solution of sodium hydrogencarbonate and saturated saline in that order, and dried with anhydrous magnesium sulfate, and the solvent was evaporated. The residue was recrystallized from ether-hexane to obtain 106 mg (yield: 50%) of 6-chloro-2,2-trimethylene-N-(2,6-diisopropylphenyl)hexanamide as colorless needle-like crystals.

Potassium carbonate (30 mg, 0.22 mmols) and 18-crown-6 (5 mg, 0.02 mmols) were added to a DMF (1 ml) solution of the resulting anilide (67 mg, 0.2 mmols) and 2-mercaptobenzoxazole (30 mg, 0.2 mmols), and stirred at 80° C. for 1 hour. The reaction mixture was diluted with water, and extracted with ether. The organic layer was washed with water, and dried with anhydrous magnesium sulfate, and the solvent was evaporated. Then, the residue was purified through preparative thin-layer chromatography (developer: hexane/acetone=5/1), and the resulting crystals were recrystallized from acetone-ether-hexane. 63 mg (yield: 68%) of the intended product was obtained as colorless needle-like crystals.

m.p.: 118°–119° C.

IR (KBr) cm$^{-1}$: 3425, 3293, 2961, 1643, 1499

$^1$-H-NMR (CDCl$_3$) δ:

1.22 (12H, d, J=6.8 Hz), 1.52–1.65 (2H, m), 1.85–2.10 (6H, m), 2.43–2.58 (2H, m), 3.07 (2H, sept, J=6.8 Hz), 3.34 (2H, t, J=6.8 Hz), 6.63 (1H, br s), 7.17 (2H, m), 7.20–7.33 (3H, m), 7.41–7.46 (1H, m), 7.57–7.62 (1H, m)

EIMS m/z (relative intensity): 464 (M$^+$, 100)

Elementary Analysis: for C$_{28}$H$_{36}$N$_2$O$_2$S

Calculated: C 72.38; H 7.81; N 6.03

Measured: C 72.50; H 7.89; N 5.87

Example 19

Production of 6-(benzoxazol-2-ylthio)-N-(2-isopropyl-6-methylphenyl)hexanamide:

DMF (catalytic amount, 1 drop) and oxalyl chloride (781 mg, 6.2 mmols) were added to a chloroform (10 ml) solution of 6-bromohexanoic acid (1.0 g, 5.1 mmols) with cooling with ice, and then stirred at room temperature for 2 hours. The reaction mixture was concentrated under reduced pressure to obtain the corresponding acid chloride.

The acid chloride prepared in the above was added to a chloroform (10 ml) solution of 2-isopropyl-6-methylaniline (765 mg, 5.1 mmols) and triethylamine (623 mg, 6.2 mmols) with cooling with ice, and stirred at room temperature for 1 hour. The reaction mixture as concentrated under reduced pressure, to which was added water. Then, this was extracted with ethyl acetate. The organic layer was washed with 1N HCl, an aqueous saturated solution of sodium hydrogencarbonate and saturated saline in that order, and dried with anhydrous magnesium sulfate, and the solvent was evaporated. The residue was purified through silica gel column chromatography (developer: hexane/ethyl acetate=4/1), and the resulting crystals were recrystallized from ethyl acetate-hexane. 983 mg (yield: 59%) of 6-bromo-N-(2-isopropyl-6-methylphenyl)hexanamide was obtained as colorless needle-like crystals.

m.p.: 66°–67° C.

IR (KBr) cm$^{-1}$: 3227, 2963, 1650, 1531, 783

$^1$H-NMR (d$_6$-DMSO) δ: 1.12 (6H, d, J=6.8 Hz), 1.41–1.58 (2H, m), 1.59–1.92 (4H, m), 1.59–1.92 (4H, m), 2.12 (3H, s), 2.25–2.38 (2H, m), 3.10 (1H, sept, J=6.8 Hz), 3.47 (1H, t, J=6.8 Hz), 3.60 (2H, t, J=6.8 Hz), 6.99–7.13 (3H, m), 7.15 (1H, br s)

Potassium carbonate (47 mg, 0.34 mmols) and 18-crown-6 (8 mg, 0.03 mmols) were added to a DMF (3 ml) solution of the resulting amide (100 mg, 0.31 mmols) and 2-mercaptobenzoxazole (46 mg, 0.31 mmols), and stirred at 80° C. for 4 hours. The reaction mixture was diluted with water, and extracted with ethyl acetate. The organic layer was washed with water, and dried with anhydrous magnesium sulfate, and the solvent was evaporated. Then, the residue was purified through silica gel column chromatography (developer: hexane/ethyl acetate=2/1), and the resulting crystals were recrystallized from ethyl acetate-hexane. 68 mg (yield: 56%) of the intended product was obtained as colorless needle-like crystals.

m.p.: 87°–88° C.

IR (KBr) cm$^{-1}$: 3246, 2965, 1645, 1500, 1454, 1132, 741

$^1$H-NMR (d$_6$-DMSO) δ: 1.12 (6H, d, J=6.8 Hz), 1.48–1.62 (2H, m), 1.63–1.78 (2H, m), 1.78–1.92 (2H, m), 2.12 (3H, s), 2.28–2.38 (2H, m), 3.11 (1H, sept, J=6.8 Hz), 3.35 (2H, t, J=7.2 Hz), 7.01 (1H, m), 7.07–7.13 (2H, m), 7.24–7.34 (2H, m), 7.53–7.61 (2H, m), 8.70 (1H, br s)

EIMS m/z (relative intensity): 396 (M$^+$)

Elementary Analysis: for C$_{23}$H$_{28}$N$_2$O$_2$S

Calculated: C 69.66; H 7.12; N 7.06

Measured: C 69.69; H 7.13; N 7.07

Example 20

Production of 6-(benzoxazol-2-ylthio)-N-(3,4,5-trimethoxyphenyl)hexanamide:

WSC (2.11 g, 11 mmols) and HOBt (1.68 g, 11 mmols) were added to a DMF (15 ml) solution of 3,4,5-trimethoxyaniline (2.75 g, 15 mmols) and 6-bromohexanoic acid (1.95 g, 10 mmols), and stirred at room temperature for 12 hours. The reaction mixture was extracted with ether. The organic layer was washed with water, 1N HCl, an aqueous saturated solution of sodium hydrogencarbonate and saturated saline in that order, and dried with anhydrous magnesium sulfate, and the solvent was evaporated. Then, the residue was purified through silica gel column chromatography (developer: hexane/acetone=5/1), and the resulting crystals were recrystallized from ether-hexane to obtain 1.42 g (yield: 40%) of 6-bromo-N-(3,4,5-trimethoxyphenyl) hexanamide as colorless needle-like crystals.

Potassium carbonate (106 mg, 0.77 mmols) and 18-crown-6 (19 mg, 0.07 mols) were added to a DMF (1.5 ml) solution of the resulting anilide (252 mg, 0.7 mmols) and 2-mercaptobenzoxazole (106 mg, 0.7 mmols), and stirred at 80° C. for 1 hour. The reaction mixture was diluted with water, and extracted with ether. The organic layer was washed with water, and dried with anhydrous magnesium sulfate, and the solvent was evaporated. Then, the residue was purified through preparative thin-layer chromatography (developer: hexane/acetone=5/2), and the resulting crystals were recrystallized from acetone-hexane. 259 mg (yield: 86%) of the intended product was obtained as colorless needle-like crystals.

m.p.: 108°–109° C.

IR (KBr) cm$^{-1}$: 3430, 3310, 1652, 1504, 1135

$^1$H-NMR (CDCl$_3$) δ: 1.52–1.65 (2H, m), 1.81 (2H, quint, J=7.3 Hz), 1.91 (2H, quint, J=7.3 Hz). 2.38 (2H, t, J=7.3 Hz), 3.32 (2H, t, J=7.3 Hz), 3.81 (3H, s), 3.82 (3H, s), 3.83 (3H, s), 6.84 (2H, s), 7.20–7.32 (2H, m), 7.33 (1H, br s), 7.45 (1H, m), 7.59 (1H, m)

EIMS m/z (relative intensity): 430 (M$^+$, 100)

Elementary Analysis: for C$_{22}$H$_{26}$N$_2$O$_5$S

Calculated: C 61.38; H 6.09; N 6.51

Measured: C 61.31; H 6.10; N 6.54

Example 21

Production of 6-(benzoxazol-2-ylsulfinyl)-N-(2,6-diisopropylphenyl)hexanamide:

m-Chloroperoxybenzoic acid (125 mg, 0.49 mmols) was added to a methylene chloride (2 ml), solution of 6-(benzoxazol-2-ylthio)-N-(2,6-diisopropylphenyl) hexanamide (258 mg, 0.61 mmols) at 0° C., and stirred for 60 minutes. The reaction mixture was diluted with an aqueous saturated solution of sodium hydrogencarbonate, and extracted with ethyl acetate. The organic layer was washed with water, and dried with anhydrous magnesium sulfate, and the solvent was evaporated. Then, the residue was purified through preparative thin-layer chromatography (developer: hexane/acetone=5/2) to obtain 179 mg (yield: 84%) of the intended product as crystals. This was recrystallized from hexane-acetone to obtain colorless needle-like crystals.

m.p.: 147°–148° C.

IR (KBr) cm$^{-1}$: 3434, 3239, 2963, 1646, 1073, 748

$^1$H-NMR (d$_6$-DMSO) δ: $^{1.26}$ (12H, d, J=6.8 Hz), 1.64–2.12 (6H, m), 2.49 (2H, m), 3.22 (2H, sept, J=6.8 Hz), 3.56 (2H, t, J=6.8 Hz), 3.59 (2H, t, J=6.8 Hz), 7.23 (1H, d, J=8.3 Hz), 7.24 (1H, d, J=7.1 Hz), 7.35 (1H, dd, J=8.3, 7.1 Hz), 7.63 (1H, td, J=7.3, 1.5 Hz), 7.68 (1H, td, J=7.3, 1.5 Hz), 7.95 (2H, ddd, J=7.3, 1.5, 0.7 Hz), 8.01 (2H, ddd, J=7.3, 1.5, 0.7 Hz), 8.84 (1H, br s)

EIMS m/z (relative intensity): 440 (M$^+$), 204 (100)

Elementary Analysis: for C$_{25}$H$_{32}$N$_2$O$_3$S

Calculated: C 68.15; H 7.32; N 6.36
Measured: C 67.97; H 7.31; N 6.29

Example 22

Production of 6-(benzoxazol-2-ylamino)-N-(2,6-diisopropylphenyl)hexanamide:

Sodium azide (195 mg, 3.0 mmols) was added to a DMF (5 ml) solution of 6-bromo-N-(2,6-diisopropylphenyl) hexanamide (354 mg, 1.0 mmol), and stirred at 100° C. for 2 hours. After having been cooled, water was added to the reaction mixture, which was then extracted with ether. The resulting extract was washed with saturated saline, and dried with anhydrous magnesium sulfate, and the solvent was evaporated to obtain 310 mg of a crude product of 6-azido-N-(2,6-diisopropylphenyl)hexanamide. This azide was all dissolved in ethanol (3 ml), to which was added 10% palladium-carbon catalyst (100 mg) and stirred in a hydrogen atmosphere for 2 hours. The reaction mixture was filtered, and the filtrate was concentrated under reduced pressure to obtain 241 mg of a crude product of 6-amino-N-(2,6-diisopropylphenyl)hexanamide.

The resulting crude amine (135 mg, 0.46 mmols) was dissolved in a mixed solvent of acetonitrile (2 ml) and DMF (1 ml), to which were added N,N-diisopropylethylamine (65 mg, 0.5 mmols) and 2-chlorobenzoxazole (71 mg, 0.46 mmols) in that order, and stirred at 90° C. for 1 hour. After having been cooled, water was added to the reaction mixture, which was then extracted with ether. The resulting extract was washed with saturated saline, and dried with anhydrous magnesium sulfate, and the solvent was evaporated. The residue was purified through preparative thin-layer chromatography (developer: hexane/acetone=5/3), and the resulting crystals were recrystallized from hexane-acetone. 96 mg (yield: 51%) of the intended product was obtained as pale brown needle-like crystals.

m.p.: 165°–166° C.

IR (KBr) cm$^{-1}$; 3231, 2965, 1678, 1648, 1461

$^1$H-NMR (d$_6$-DMSO) δ: 1.11 (12H, d, J=6.8 Hz), 1.40–1.56 (2H, m), 1.61–1.75 (4H, m), 2.28–2.40 (2H, m), 3.08 (2H, sept, J=6.8 Hz), 3.34 (2H, quint, J=6.5 Hz), 6.92 (1H, dt, J=7.8, 1.5 Hz), 7.06 (1H, dt, J=7.8, 1.5 Hz), 7.05–7.12 (2H, m), 7.19 (1H, dd, J=8.5, 6.8 Hz), 7.19 (1H, ddd, J=7.8, 1.5, 0.5 Hz), 7.23 (1H, ddd, J=7.8, 1.5, 0.5 Hz), 7.32 (1H, m), 8.66 (1H, br s)

EIMS m/z (relative intensity): 407 (M$^+$, 100)

Elementary Analysis: for C$_{25}$H$_{33}$N$_3$O$_2$

Calculated: C 73.68; H 8.16; N 10.31

Measured: C 73.65; H 8.34; N 10.19

Example 23

Production of 2-(benzimidazol-2-ylthio)-N-(2,6-diisopropylphenyl)acetamide:

According to the same process as in Example 1, the intended product was obtained as colorless needle-like crystals.

m.p.: 223°–225° C.

IR (KBr) cm$^{-1}$: 3272, 2963, 1665, 1135, 742

$^1$H-NMR (d$_6$-DMSO) δ: 1.07 (12H, d, J=6.8 Hz), 3.09 (2H, sept, J=6.8 Hz), 4.20 (2H, s), 7.09–7.17 (4H, m), 7.23 (1H, dd, J=8.5, 6.8 Hz), 7.42–7.48 (2H, m), 9.33 (1H, br s)

EIMS m/z (relative intensity): 367 (M$^+$), 217 (100)

Elementary Analysis: for C$_{21}$H$_{25}$N$_3$OS

Calculated: C 68.63; H 6.86; N 11.43; S 8.72

Measured: C 68.75; H 7.02; N 11.35; S 8.67

Example 24

Production of 4-(benzimidazol-2-ylthio)-N-(2,6-diisopropylphenyl)butanamide:

According to the same process as in Example 3, the intended product was obtained as colorless needle-like crystals.

m.p.: 214°–215° C.

IR (KBr) cm$^{-1}$: 3393, 3253, 1651, 1439, 1401

$^1$H-NMR (d$_6$-DMSO) δ: 1.22 (12H, d, J=6.8 Hz), 2.16–2.28 (2H, m), 2.55–2.70 (2H, m), 3.18 (2H, sept, J=6.8 Hz), 3.48 (2H, t, J=7.3 Hz), 7.15–7.24 (4H, m), 7.32 (1H, dd, J=8.5, 6.8 Hz), 7.41–7.55 (2H, m), 8.98 (1H, br s)

EIMS m/z (relative intensity): 395 (M$^+$), 150 (100)

Elementary Analysis: for C$_{23}$H$_{25}$N$_3$OS•0.17 H$_2$O

Calculated: C 69.31; H 7.42; N 10.54

Measured: C 69.13; H 7.31; N 10.37

Example 25

Production of 5-(benzimidazol-2-ylthio)-N-(2,6-diisopropylphenyl)pentanamide:

According to the same process as in Example 4, the intended product was obtained as colorless needle-like crystals.

m.p.: 208°–209° C.

IR (KBr) cm$^{-1}$: 3383, 3270, 1653, 1518, 1401

$^1$H-NMR (d$_6$-DMSO) δ: 1.19 (12H, d, J=6.8 Hz), 1.86–1.98 (4H, m), 2.45–1.53 (2H, m), 3.16 (2H, sept, J=6.8 Hz), 3.43 (2H, t, J=6.8 Hz), 7.13–7.21 (4H, m), 7.29 (1H, dd, J=8.5, 6.8 Hz), 7.45–7.53 (2H, m), 8.82 (1H, br s)

EIMS m/z (relative intensity): 409 (M$^+$, 100)

Elementary Analysis: for C$_{24}$H$_{31}$N$_3$OS

Calculated: C 70.38; H 7.63; N 10.26

Measured: C 70.16; H 7.75; N 10.26

Example 26

Production of 6-(benzimidazol-2-ylthio)-N-(2,6-diisopropylphenyl)hexanamide:

According to the same process as in Example 5, the intended product was obtained as colorless needle-like crystals.

m.p.: 204°206° C.

IR (KBr) cm$^{-1}$: 3240, 2963, 1647, 1268, 739

$^1$H-NMR (d$_6$-DMSO) δ: 1.18 (12H, d, J=6.8 Hz), 1.62 (2H, m), 1.83 (2H, m), 2.44 (2H, t, J=7.3 Hz), 3.06 (2H, sept, J=6.8 Hz), 3.26 (2H, t, J=7.3 Hz), 7.15–7.32 (7H, m)

EIMS m/z (relative intensity): 423 (M$^+$, 100)

Elementary Analysis: for C$_{25}$H$_{33}$N$_3$OS•0.1H$_2$O

Calculated: C 70.58; H 7.87; N 9.88; S 7.57

Measured: C 70.49; H 7.93; N 9.63; S 7.38

Example 27

Production of 7-(benzimidazol-2-ylthio)-N-(2,6-diisopropylphenyl)heptanamide:

According to the same process as in Example 6, the intended product was obtained as colorless needle-like crystals.

m.p.: 164–165° C.

IR (KBr) cm$^{-1}$: 3424, 3273, 1648, 1515, 1443

¹H-NMR (d₆-DMSO) δ: 1.27 (12H, d, J=6.8 Hz), 1.54–1.99 (8H, m), 2.43–2.54 (2H, m), 3.24 (2H, sept, J=6.8 Hz), 3.43 (2H, t, J=7.3 Hz), 7.20–7.30 (4H, m), 7.35 (1H, dd, J =8.5, 6.8 Hz), 7.52–7.58 (2H, m), 8.83 (1H, br s)

EIMS m/z (relative intensity): 437 (M⁺, 100)

Elementary Analysis: for $C_{26}H_{35}N_3OS$ Calculated: C 71.36; H 8.06; N 9.60 Measured: C 71.19; H 8.33; N 9.30

Example 28

Production of 8-(benzimidazol-2-ylthio)-N-(2,6-diisopropylphenyl)octanamide

According to the same process as in Example 7, the intended product was obtained as colorless needle-like crystals.

m.p.: 129–130° C.

IR (KBr) cm⁻¹: 3381, 3235, 2962, 1651, 1439

¹H-NMR (d₆-DMSO) δ: 1.28 (12H, d, J=6.8 Hz), 1.50–1.95 (10H, m), 2.46–2.53 (2H, m), 3.25 (2H, sept, J=6.8 Hz), 3.44 (2H, t, J=7.3 Hz), 7.21–7.28 (4H, m), 7.36 (1H, dd, J=8.5, 6.8 Hz) 7.55 (2H, m), 8.81 (1H, br s)

EIMS m/z (relative intensity): 451 (M⁺, 100)

Elementary Analysis: for $C_{27}H_{37}N_3OS$ Calculated: C 71.80; H 8.26; N 9.30 Measured: C 71.65; H 8.26; N 9.23

Example 29

Production of 9-(benzimidazol-2-ylthio)-N-(2,6-diisopropylphenyl)nonanamide

According to the same process as in Example 9, the intended product was obtained as colorless needle-like crystals.

m.p.: 159–160° C.

IR (KBr) cm⁻¹: 3422, 3278, 2930, 1648, 1403

¹H-NMR (d₆-DMSO) δ: 1.29 (12H, d, J=6.8 Hz), 1.49–2.00 (12H, m), 2.45–2.55 (2H, m), 3.25 (2H, sept, J=6.8 Hz), 3.44 (2H, t, J=7.3 Hz), 7.21–7.30 (4H, dd, J=8.5, 6.8 Hz), 7.52–7.58 (2H, m), 8.82 (1H, br s)

EIMS m/z (relative intensity): 465 (M⁺, 100)

Elementary Analysis: for $C_{28}H_{39}N_3OS$ Calculated: C 72.22; H 8.44; N 9.02 Measured: C 72.38; H 8.65; N 8.88

Example 30

Production of 10-(benzimidazol-2-ylthio)-N-(2,6-diisopropylphenyl)decanamide

According to the same process as in Example 9, the intended product was obtained as colorless needle-like crystals.

m.p.: 137–138° C.

IR (KBr) cm⁻¹: 3385, 3276, 2928, 1651, 1440

¹H-NMR (d₆-DMSO) δ: 1.29 (12H, d, J=6.8 Hz), 1.42 –1.99 (14H, m), 2.43 –2.55 (2H, m), 3.26 (2H, sept, J =6.8 Hz), 3.43 (2H, t, J=7.3 Hz), 7.21–7.30 (4H, m), 7.37 (1H, dd, J=8.5, 6.8 Hz), 7.53–7.62 (4H, m), 8.82 (1H, br s)

EIMS m/z (relative intensity): 479 (M⁺, 100)

Elementary Analysis: for $O_{29}H_{41}N_3OS$

Calculated: C 72.61; H 8.61; N 8.76

Measured: C 72.71; H 8.87; N 8.57

Example 31

Production of 15-(benzimidaxol-2-ylthio)-N-(2,6-diisopropylphenyl)pentadecanamide According to the same process as in Example 10, the intended product was obtained as colorless needle-like crystals.

m.p.: 72–74° C.

IR (KBr) cm⁻¹: 3428, 3234, 1652, 1526, 1438

H-NMR (d₆-DMSO) δ: 1.29 (12H, d, J =6.8 Hz), 1.40–1.95 (24H, m), 2.44–2.53 (2H, m), 3.26 (2H, sept, J=6.8 Hz), 3.42 (2H, t, J=7.3 Hz), 7.21–7.28 (5H, m), 7.36 (1H, dd, J=8.5, 6.8 Hz), 7.53–7.60 (2H, m), 8.83 (1H, br s)

EIMS m/z (relative intensity): 549 (M⁺100)

Elementary Analysis: for $C_{34}H_{51}N_3OS$ Calculated: C 74.27; H 9.35; N 7.64 Measured: C 74.05; H 9.35; N 7.61

Example 32

Production of 2-(benzimidazol-2-ylthio)-N-(2,4-difluorophenyl)acetamide

According to the same process as in Example 11, the intended product was obtained as colorless needle-like crystals.

m.p.: 183–184° C.

IR (KBr) cm⁻¹: 3387, 3158, 1661, 1571, 1503

¹H-NMR (CDCl₃) δ: 4.05 (2H, s), 6.79–6.89 (2H, m), 7.19–7.28 (2H, m), 7.40 (1H, br), 7.64 (1H, br), 8.19 (1H, m)

EIMS m/z (relative intensity): 319 (M⁺, 100)

Elementary Analysis: for $C_{15}H_{11}F_2N_3OS \cdot 0.1H_2O$ Calculated: C 56.10; H 3.52; N 13.08 Measured: C 56.05; H 3.49; N 13.01

Example 33

Production of 4-(benzimidazol-2-ylthio)-N-(2,4-difluorophenyl)butanamide

According to the same process as in Example 12, the intended product was obtained as colorless needle-like crystals.

m.p.: 143–145° C.

IR (KBr) cm⁻¹: 3290, 3154, 1665, 1527, 1513

¹H-NMR (CDCl₃) δ: 216 (2H, quint, J=7.3 Hz), 2.62 (2H, t, J=7.3 Hz), 3.31 (2H, t, J=7.3 Hz), 6.82–6.91 (2H, m), 7.14–7.25 (4H, m), 7.43–7.50 (2H, m), 7.90–8.02 (1H, m)

EIMS m/z (relative intensity): 347 (M⁺), 150 (100)

Elementary Analysis: for $C_{17}H_{15}F_2N_3OS \cdot 0.1H_2O$ Calculated: C 56.10; H 3.52; N 13.08 Measured: C 56.05; H 3.49; N 13.01

Example 34

Production of 5-(benzimidazol-2-ylthio)-N-(2,3-difluorophenyl)pentanamide

According to the same process as in Example 13, the intended product was obtained as colorless needle-like crystals.

m.p.: 133–134° C.

IR (KBr) cm⁻¹: 3309, 1665, 1541, 1429, 1406

¹H-NMR (CDCl₃)δ: 1.83–1.95 (4H, m), 2.45 (2H, t, J=7.3 Hz), 3.31 (2H, t, J=7.3 Hz), 6.79–6.89 (2H, m), 7.15–7.22 (2H, m), 7.51 (1H, m), 8.08–8.16 (1H, m), 10.01 (1H, br s)

EIMS m/z (relative intensity): 361 (M⁺, 100)

Elementary Analysis: for $C_{18}H_{17}F_2N_3OS$ Calculated: C 59.82; H 4.74; N 11.63 Measured: C 59.79; H 4.67; N 11.58

Example 35

Production of 6(benzimidazol-2-ylthio)-N-(2,4-difluorophenyl)hexanamide

According to the same process as in Example 14, the intended product was obtained as colorless needle-like crystals.

m.p.: 161–162° C.

IR (KBr) cm$^{-1}$: 3271, 2983, 1664, 1531, 1513

$^1$H-NMR (CDCl$_3$-d$_4$-MeOH) δ: 1.52–1.61 (2H, m), 1.69–1.82 (4H, m), 2.41 (2H, t, J=7.3 Hz), 3.24 (2H, t, J=7.3 Hz), 6.81–6.90 (2H, m), 7.15–7.22 (2H, m), 7.40–7.55 (2H, m), 7.88–7.98 (1H, m), 8.80 (1H, br s)

EIMS m/z (relative intensity): 375 (M$^+$, 100)

Elementary Analysis: for C$_{19}$H$_{19}$F$_2$N$_3$OS Calculated: C 60.79; H 5.10; N 11.19 Measured: C 60.75; H 5.19; N 11.08

Example 36

Production of 10-(benzimidazol-2-ylthio)-N-(2,4-difluorophenyl)decanamide

According to the same process as in Example 15, the intended product was obtained as colorless needle-like crystals.

m.p.: 116–117° C

IR (KBr) cm$^{-1}$: 3436, 3279, 1668, 1531, 1430

$^1$H-NMR (CDCl$_3$) δ: 1.20–1.48 (10H, m), 1.56–1.79 (4H, m), 2.39 (2H, t, J=7.3 Hz), 3.32 (2H, t, J=7.3 Hz), 6.81–6.91 (2H, m), 7.15–7.22 (2H, m), 7.32 (1H, br s), 7.65 (2H, br s), 8.18–8.29 (1H, m), 9.56 (1H, br s)

EIMS m/z (relative intensity): 431 (M$^+$), 150 (100)

Elementary Analysis: for C$_{23}$H$_{27}$F$_2$N$_3$OS Calculated: C 64.02; H 6.31; N 9.74 Measured: C 63.99; H 6.34; N 9.64

Example 37

Production of 5-(benzimidazol-2-ylthio)-N-(2,6-difluorophenyl)-2,2-dimethylpentanamide According to the same process as in Example 16, the intended product was obtained as colorless needle-like crystals.

m.p.: 195–197° C.

IR (KBr) cm$^{-1}$: 3191, 2963, 1636, 1269, 740

$^1$H-NMR (d$_6$-DMSO) δ: 1.11 (12H, d, J=6.8 Hz), 1.28 (6H, s), 1.73–1.92 (4H, m), 3.07 (2H, sept, J=6.8 Hz), 3.32 (2H, m), 7.05–7.53 (7H, m), 8.41 (1H, br s)

EIMS m/z (relative intensity): 437 (M$^+$, 100)

Elementary Analysis: for C$_{26}$H$_{35}$N$_3$OS·0.25H$_2$O Calculated: C 70.63; H 8.09; N 9.50 Measured: C 70.58; H 8.10; N 9.24

Example 38

Production of 6-(benzimidazol-2-ylthio)-N-(2-isopropyl-6-methylphenyl)hexanamide According to the same process as in Example 19, the intended product was obtained as colorless needle-like crystals.

m.p.: 138–140° C.

IR (KBr) cm$^{-1}$: 3241, 2961, 1651, 1437, 1286, 743

$^1$H-NMR (d$_6$-DMSO) δ: 1.12 (6H, d, J=6.8 Hz), 1.47–1.62 (2H, m), 1.62–1.85 (4H, m), 2.12 (3H, s), 2.28–2.40 (2H, m), 3.11 (1H, sept, J=6.8 Hz), 3.28 (2H, t, J=7.2 Hz), 6.98–7.12 (6H, m), 7.33 (1H, m), 7.46 (1H, m), 8.69 (1H, br s)

EIMS m/z (relative intensity): 395 (M$^+$)

Elementary Analysis: for C$_{23}$H$_{29}$N$_3$OS Calculated: C 69.84; H 7.39; N 10.62 Measured: C 69.82; H 7.44; N 10.71

Example 39

Production of 6-(benzimidazol-2-ylthio)-N-(3,4,5-trimethoxyphenyl)hexanamide

According to the same process as in Example 20, the intended product was obtained as colorless needle-like crystals.

m.p.: 162–163° C.

IR (KBr) cm$^{-1}$: 3170, 2933, 1660, 1509, 1453

$^1$H-NMR (CDCl$_3$): δ: 1.44–1.57 (2H, m), 1.66–1.86 (4H, m), 2.33 (2H, t, J=7.3 Hz), 3.24 (2H, t, J=7.3 Hz), 3.76 (6H, s), 3.81 (3H, s), 6.91 (2H, s), 7.17–7.25 (2H, m), 7.36 (1H, m), 7.65 (1H, m), 8.17 (1H, br s), 9.84 (1H, br s)

EIMS m/z (relative intensity): 429 (M$^+$, 100)

Elementary Analysis: for C$_{22}$H$_{27}$N$_3$O$_4$S Calculated: C 61.52; H 6.34; N 9.78 Measured: C 61.44; H 6.37; N 9.79

Example 40

Production of 6(benzimidazol-2-ylsulfinyl)-N-(2,6-diisopropylphenyl)hexanamide m-Chloroperoxybenzoic acid (70 mg, 0.27 mols) was added to a methylene chloride-methanol (2/1, 3 ml) solution of 6-(benzimidazol-2-ylthio)-N-(2,6-diisopropylphenyl)hexanamide as obtained in Example 26, at −78° C., and stirred for 10 minutes. The reaction mixture was diluted with an aqueous saturated solution of sodium hydrogencarbonate, and extracted with ethyl acetate. The organic layer was washed with water, and dried with anhydrous magnesium sulfate, and the solvent was evaporated. The residue was purified through partitioning thin-layer chromatography (developer: hexane/acetone=5/3) to obtain 35 mg (yield: 23%) of crystals, which were then recrystallized from hexane-acetone to obtain the intended product as colorless needle-like crystals.

m.p.: 187–188° C.

IR (KBr) cm$^{-1}$: 3428, 3216, 2962, 1647, 1075, 738

$^1$H-NMR (d$_6$-DMSO) δ: 1.27 (12H, d, J=6.8 Hz), 1.64–2.07 (6H, m), 2.49 (2H, m), 3.23 (2H, sept, J=6.8 Hz), 3.33–3.56 (2H, m), 7.24 (1H, d, J=8.3 Hz), 7.25 (1H, d, J=7.1 Hz), 7.36 (1H, dd, J=8.3, 7.1 Hz), 7.42 (1H, dd, J=7.1, 6.1 Hz), 7.45 (1H, dd, J=7.1, 6.1 Hz), 7.46–7.83 (2H, m), 8.84 (1H, br s)

EIMS m/z (relative intensity): 439 (M$^+$), 204 (100)

Elementary Analysis: for C$_{25}$H$_{33}$N$_3$O$_2$S Calculated: C 68.30; H 7.57; N 9.56 Measured: C 68.01; H 7.62; N 9.37

Example 41

Production of 6-(benzimidazol-2-ylsulfonyl)-N-(2,6-diisopropylphenyl)hexanamide:

35 mg (yield: 23%) of crystals as obtained at the same time in Example 40 were recrystallized from hexane-acetone. Thus was obtained the intended product as colorless needle-like crystals.

m.p.: 207–208° C.

IR (KBr) cm$^{-1}$: 3421, 3245, 2962, 1640, 1140

$^1$H-NMR (d$_6$-DMSO) δ: 1.12 (12H, d, J=6.8 Hz), 1.43–1.90 (6H, m), 2.32 (2H, m), 3.04 (2H, sept, J=6.8 Hz), 3.55 (2H, t, J=7.6 Hz), 7.09 (1H, d, J=8.3 Hz), 7.10 (1H, d, J=7.1 Hz), 7.21 (1H, dd, J=8.3, 7.1 Hz), 7.33–7.42 (2H, m), 7.67–7.74 (2H, m), 7.46–7.83 (2H, m), 8.69 (1H, br s)

EIMS m/z (relative intensity): 455 (M$^+$, 100)

Elementary Analysis: for C$_{25}$H$_{33}$N$_3$O$_3$S·0.3H$_2$O Calculated: C 65.13; H 7.35; N 9.11 Measured: C 65.16; H 7.36; N 8.92

Example 42

Production of 2-(benzothiazol-2-ylthio)-N-(2,6-diisopropylphenyl)acetamide

According to the same process as in Example 1, the intended product was obtained as colorless needle-like crystals.

m.p.: 130–133° C.

IR (KBr) cm$^{-1}$: 3353, 2961, 1662, 1508, 765

$^1$H-NMR (d6-DMSO) δ: 1.08 (12H, d, J=6.8 Hz), 3.10 (2H, sept, J=6.8 Hz), 4.34 (2H, s), 7.11 (1H, d, J=8.3 Hz), 7.12 (1H, d, J=7.3 Hz), 7.23 (1H, dd, J=8.3, 7.3 Hz), 7.46 (1H, td, J=7.8, 1.2 Hz), 7.51 (1H, td, J=7.8, 1.2 Hz), 7.87 (1H, dd, J=7.8, 1.2 Hz), 7.98 (1H, dd, J=7.8, 1.2 Hz)

EIMS m/z (relative intensity): 384 (M$^+$), 217 (100)

Elementary Analysis: for $C_{21}H_{24}N_2OS_2$ Calculated: C 65.69; H 6.29; N 7.28; S 16.67 Measured: C 65.41; H 6.47; N 7.21; S 16.38

Example 43

Production of 3-(benzothiazol-2-ylthio)-N-(2,6-diisopropylphenyl)propanamide

According to the same process as in Example 2 the intended product was obtained as colorless needle-like crystals.

m.p.: 153–154° C.

IR (KBr) cm$^{-1}$: 3432, 3240, 1654, 1527, 1428

$^1$H-NMR (d$_6$-DMSO) δ: 1.14 (12H, d, J=6.8 Hz), 2.94 (2H, t, J=6.8 Hz), 3.13 (2H, sept, J=6.8 Hz), 3.67 (2H, t, J=6.8 Hz), 7.1–7.16 (2H, m), 7.23 (1H, dd, J=8.5, 6.8 Hz), 7.35 (1H, ddd, J=8.0, 7.3, 1.5 Hz), 7.46 (1H, ddd, J=8.0, 7.3, 1.5 Hz), 7.85 (1H, ddd, J=8.0, 1.5, 1.2 Hz), 7.95 (1H, ddd, J=8.0, 1.5, 1.2 Hz), 8.95 (1H, br s)

EIMS m/z (relative intensity): 398 (M$^+$), 167 (100)

Elementary Analysis: for $C_{22}H_{26}N_3O_2S$ Calculated: C 66.30; H 6.57; N 7.03 Measured: C 66.60; H6.76; N 6.93

Example 44

Production of 4-benzothiazol-2-ylthio)-N_(2,6-diisopropylphenyl)butanamide:

According to the same process as in Example 3, the intended product was obtained as colorless needle-like crystals.

m.p.: 137–138° C.

IR (KBr) cm$^{-1}$: 3445, 3231, 1653, 1534, 1431

$^1$H-NMR (d$_6$-DMSO) δ: 1.13 (12H, d, J=6.8 Hz), 2.13–2.25 (2H, m), 2.50–2.64 (2H, m), 3.10 (2H, sept, J=6.8 Hz), 3.47 (2H, t, J=7.3 Hz), 7.12 (2H, m), 7.22 (1H, dd, J=8.5, 6.8 Hz), 7.35 (1H, ddd, J=7.3, 1.5, 1.2 Hz), 7.46 (1H, ddd, J=7.3, 1.5, 1.2 Hz), 7.83 (1H, ddd, J=8.0, 1.5, 1.2 Hz), 7.95 (1H, ddd, J=7.3, 1.5, 1.2 Hz), 8.85 (1H, br s)

EIMS m/z (relative intensity): 412 (M$^+$), 235 (100)

Elementary Analysis: for $C_{23}H_{28}N_2OS_2$

Calculated: C 66.95; H 6.84; N 6.79

Measured: C 67.02; H 6.92; N 6.87

Example 45

Production of 5-(benzothiazol-2-ylthio)-N-(2,6-diisopropylphenyl)pentanamide:

According to the same process as in Example 4, the intended product was obtained as colorless needle-like crystals.

m.p.: 132–133° C.

IR (KBr) cm$^{-1}$: 3423, 3245, 1651, 1527, 1428

$^1$H-NMR (d$_6$-DMSO) δ: 1.12 (12H, d, J=6.8 Hz), 1.80–1.98 (4H, m), 2.40–2.49 (2H, m), 3.09 (2H, sept, J=6.8 Hz), 3.44 (2H, t, J=6.8 Hz), 7.11 (2H, m), 7.22 (1H, dd, J=8.5, 6.8 Hz), 7.36 (1H, ddd, J=7.3, 1.5, 1.2 Hz), 7.46 (1H, ddd, J=7.3, 1.5, 1.2 Hz), 7.86 (1H, ddd, J=8.0, 1.2, 0.7 Hz), 7.95 (1H, ddd, J=7.3, 1.2, 0.7 Hz), 8.76 (1H, br s)

EIMS m/z (relative intensity): 426 (M$^+$, 100)

Elementary Analysis: for $C_{24}H_{30}N_2OS_2$

Calculated: C 67.57; H 7.09; N 6.57

Measured: C 67.42; H 7.23; N 6.65

Example 46

Production of 6-(benzothiazol-2-ylthio)-N-(2,6-diisopropylphenyl)hexanamide:

According to the same process as in Example 5, the intended product was obtained as colorless needle-like crystals.

m.p.: 110–112° C.

IR (KBr) cm$^{-1}$: 3232, 2961, 1648, 1426, 997

$^1$H-NMR (d$_6$-DMSO) δ: 1.14 (12H, d, J=6.8 Hz), 1.51–1.96 (6H, m), 2.48 (2H, m), 3.11 (2H, sept, J=6.8 Hz), 3.40 (2H, t, J=7.1 Hz), 7.11 (1H, t, J=8.3 Hz), 7.12 (1H, d, J=7.1 Hz), 7.22 (1H, dd, J=8.3, 7.1 Hz), 7.35 (1H, td, J=7.8, 1.2 Hz), 7.46 (1H, td, J=7.8, 1.2 Hz), 7.84 (1H, ddd, J=7.8, 1.2, 0.7 Hz), 7.94 (1H, ddd, J=7.8, 1.2, 0.7 Hz), 8.72 (1H, br s)

EIMS m/z (relative intensity: 440 (M$^+$, 100)

Elementary Analysis: for $C_{25}H_{32}N_2SO_2$

Calculated: C 68.14; H 7.32; N 6.36; S 14.55

Measured: C 68.03; H 7.40; N 6.33; S 14.76

Example 47

Production of 7-(benzothiazol-2-ylthio)-N-(2,6-diisopropylphenyl)heptanamide:

According to the same process as in Example 6, the intended product was obtained as colorless needle-like crystals.

m.p.: 102–103° C.

IR (KBr) cm$^{-1}$: 3443, 3247, 1645, 1529, 1428

$^1$H-NMR (d$_6$-DMSO) δ: 1.26 (12H, d, J=6.8 Hz), 1.56–2.04 (8H, m), 2.46–2.54 (2H, m), 3.23 (2H, sept, J=6.8 Hz), 3.51 (2H, t, J=7.5 Hz), 7.24 (2H, m), 7.34 (1H, dd, J=8.5, 6.8 Hz), 7.47 (1H, ddd, J=7.3, 1.5, 1.2 Hz), 7.57 (1H, ddd, J=7.3, 1.5, 1.2 Hz), 7.97 (1H, ddd, J=8.0, 1.2, 0.7 Hz), 8.06 (1H, ddd, J=8.0, 1.2, 0.7 Hz), 8.79 (1H, br s)

EIMS m/z (relative intensity): 454 (M$^+$, 100)

Elementary Analysis: for $C_{26}H_{34}N_2OS_2$

Calculated: C 68.68; H 7.54; N 6.16

Measured: C 68.63; H 7.75; N 6.15

Example 48

Production of 8-(benzothiazol-2-ylthio)-N-(2,6-diisopropylphenyl)octanamide:

According to the same process as in Example 7, the intended product was obtained as colorless needle-like crystals.

m.p.: 91–93° C.

IR (KRr) cm$^{-1}$: 3435, 3234, 1652, 1523, 1428

$^1$H-NMR (d$_6$-DMSO) δ: 1.27 (12H, d, J=6.8 Hz), 1.52–2.05 (10H, m), 2.45–2.53 (2H, m), 3.24 (2H, sept, J=6.8 Hz), 3.52 (2H, t, J=7.3 Hz), 7.25 (2H, m), 7.35 (1H, dd, J=8.5, 6.8 Hz), 7.49 (1H, ddd, J=7.3, 1.5, 1.2 Hz), 7.59 (1H, ddd, J=7.3, 1.5, 1.2 Hz), 7.97 (1H, ddd, J=8.0, 1.2, 0.7 Hz), 8.08 (1H, ddd, J=7.3, 1.2, 0.7 Hz), 8.81 (1H, br s)

EIMS m/z (relative intensity): 468 (M+, 100)

Elementary Analysis: for $C_{27}H_{36}N_2OS_2$

Calculated: C 69.19; H 7.74; N 5.98

Measured: C 69.23; H 7.93; N 5.84

Example 49

Production of 9-(benzothiazol-2-ylthio)-N-(2,6-diisopropylphenyl)nonanamide:

According to the same process as in Example 8, the intended product was obtained as colorless needle-like crystals.

m.p.: 87–88° C.

IR (KBr) cm$^{-1}$: 3448, 3284, 1651, 1518, 1428

$^1$H-NMR (d$_6$-DMSO) δ: 1.28 (12H, d, J=6.8 hz), 1.50–2.05 (12H, m) 2.43–2.56 (2H, m), 3.25 (2H, sept, J=6.8 Hz), 3.52 (2H, t, J=7.3 Hz), 7.26 (2H, m), 7.36 (1H, dd, J=8.5, 6.8 Hz), 7.49 (1H, ddd, J=7.3, 1.5, 1.2 Hz), 7.60 (1H, ddd, J=7.3, 1.5, 1.2 Hz), 7.98 (1H, ddd, J=8.0, 1.2, 0.7 Hz), 8.09 (1H, ddd, J=7.3, 1.2, 0.7 Hz), 8.82 (1H, br s)

EIMS m/z (relative intensity): 482 (M+, 100)

Elementary Analysis: for $C_{28}H_{38}N_2OS_2$

Calculated: C 69.67; H 7.93; N 5.80

Measured: C 69.68; H 8.03; N 5.80

Example 50

Production of 10-(benzothiazol-2ylthio)-N-(2,6-diisopropylphenyl)decanamide:

According to the same process as in Example 9, the intended product was obtained as colorless needle-like crystals.

m.p.: 50–51° C.

IR (KBr) cm$^{-1}$: 3433, 3253, 1649, 1527, 1428

$^1$H-NMR (d$_6$-DMSO) δ: 1.29 (12H, d, J=6.8 Hz), 1.45–2.05 (14H, m), 2.44–2.56 (2H, m), 3.25 (2H, sept, J=6.8 Hz), 3.52 (2H, t, J=7.3 Hz), 7.26 (2H, m), 7.37 (1H, dd, J=8.5, 6.8 Hz), 7.49 (1H, ddd, J=7.3, 1.5, 1.2 Hz), 7.60 (1H, ddd, J=7.3, 1.5, 1.2 Hz), 7.98 (1H, ddd, J=8.0, 1.2, 0.7 Hz), 8.09 (1H, ddd, J=7.3, 1.2, 0.7 Hz), 8.82 (1H, br s)

EIMS m/z (relative intensity): 496 (M+), 204 (100)

Elementary Analysis: for $C_{29}H_{40}N_2OS_2$

Calculated: C 70.12; H 8.12; N 5.64

Measured: C 70.06; H 8.37; N 5.57

Example 51

Production of 15-(benzothiazol-2-ylthio)-N-(2,6-diisopropylphenyl)pentadecanamide:

According to the same process as in Example 10, the intended product was obtained as colorless needle-like crystals.

m.p.: 40–42° C.

IR (KBr) cm$^{-1}$: 3436, 3233, 1645, 1523, 1428

$^1$H-NMR (d$_6$-DMSO) δ: 1.29 (12H, d, J=6.8 Hz), 1.40–1.87 (22H, m), 1.96 (2H, quint, J=7.3 Hz), 2.43–2.52 (2H, m), 3.25 (2H, sept, J=6.8 Hz), 3.51 (2H, t, J=7.3 Hz), 7.23–7.29 (2H, m), 7.36 (1H, dd, J=8.5, 6.8 Hz), 7.49 (1H, ddd, J=8.0, 7.3, 1.5 Hz), 7.59 (1H, ddd, J=8.0, 7.3, 1.5 Hz), 7.98 (1H, ddd, J=8.0, 1.5, 1.2 Hz), 8.08 (1H, ddd, J=8.0, 1.5, 1.2 Hz), 8.83 (1H, br s)

EIMS m/z (relative intensity): 566 (M+, 100)

Elementary Analysis: for $C_{34}H_{50}N_2OS_2$

Calculated: C 72.04; H 8.89; N 4.94

Measured: C 71.92, H 8.96; N 4.89

Example 52

Production of 2-(benzothiazol-2-ylthio)-N-(2,4-difluorophenyl)acetamide:

According to the same process as in Example 11, the intended product was obtained as colorless needle-like crystals.

m.p.: 133–134° C.

IR (KBr) cm$^{-1}$: 3265, 1684, 1557, 1501, 1431

$^1$H-NMR (CDCl$_3$) δ: 4.09 (2H, s), 6.76–6.89 (2H, m), 7.37 (1H, ddd, J=8.0, 7.3, 1.5 Hz), 7.50 (1H, ddd, J=8.0, 7.3, 1.5 Hz), 7.78 (1H, ddd, J=8.0, 0.7, 0.5 Hz), 7.98 (1H, br d, J=8.0 Hz), 8.36 (1H, m), 10.46 (1H, br s)

EIMS m/z (relative intensity): 336 (M+), 208 (100)

Elementary Analysis: for $C_{15}H_{10}F_2N_2OS_2$

Calculated: C 53.56; H 3.00; N 8.33

Measured: C 53.53; H 3.07; N 8.29

Example 53

Production of 4-(benzothiazol-2-ylthio)-N-(2,4-difluorophenyl)butanamide:

According to the same process as in Example 12, the intended product was obtained as colorless needle-like crystals.

m.p.: 89–90° C.

IR (KBr) cm$^{-1}$: 3427, 3269, 1664, 1534, 1428

$^1$H-NMR (CDCl$_3$) δ: 2.30 (2H, quint, J=6.8 Hz), 2.63 (2H, t, J=6.8 Hz), 3.50 (2H, t, J=6.8 Hz), 6.81–6.92 (2H, m), 7.29 (1H, ddd, J=8.0, 7.3, 1.5 Hz), 7.39 (1H, ddd, J=8.0, 7.3, 1.5 Hz), 7.63 (1H, br s), 7.72–7.78 (2H, m), 8.20 (1H, m)

EIMS m/z (relative intensity): 364 (M+), 235 (100)

Elementary Analysis: for $C_{17}H_{14}F_2N_2OS_2$

Calculated: C 56.03; H 3.87; N 7.69

Measured: C 56.02; H 3.93; N 7.68

Example 54

Production of 5-(benzothiazol-2-ylthio)-N-(2,4-difluorophenyl)pentanamide:

According to the same process as in Example 13, the intended product was obtained as colorless needle-like crystals.

m.p.: 153–154° C.

IR (KBr) cm$^{-1}$: 3435, 3257, 1665, 1509, 1429

$^1$H-NMR (CDCl$_3$-d$_4$-MeOH) δ: 1.88–1.96 (4H, m), 2.45–2.52 (2H, m), 3.35–3.41 (2H, m), 6.81–6.90 (2H, m), 7.31 (1H, ddd, J=7.3, 1.5, 1.2 Hz), 7.43 (1H, ddd, J=7.3, 1.5, 1.2 Hz), 7.77 (1H, ddd, J=8.0, 1.5, 1.2 Hz), 7.84 (1H, ddd, J=8.0, 1.5, 1.2 Hz), 7.99 (1H, m), 8.53 (1H, br s)

EIMS m/z (relative intensity): 378 (M+, 100)

Elementary Analysis: for $C_{18}H_{16}F_2N_2OS_2$

Calculated: C 57.13; H 4.26; N 7.40

Measured: C 57.22; H 4.30; N 7.30

Example 55

Production of 6-(benzothiazol-2-ylthio)-N-(2,4-difluorophenyl)hexanamide:

According to the same process as in Example 14, the intended product was obtained as colorless needle-like crystals.

m.p.: 82–83° C.

IR (KBr) cm$^{-1}$: 3281, 1662, 1530, 1460, 1428

$^1$H-NMR (CDCl$_3$) δ: 1.53–1.65 (2H, m), 1.75–1.95 (4H, m), 2.42 (2H, t, J=7.3 Hz), 3.37 (2H, t, J=7.3 Hz), 6.80–6.91 (2H, m), 7.20 (1H, br s), 7.29 (1H, ddd, J=7.3, 1.4, 0.7 Hz), 7.40 (1H, ddd, J=7.3, 1.4, 0.7 Hz), 7.75 (1H, ddd, J=7.3, 1.4, 0.5 Hz), 7.85 (1H, ddd, J=7.3, 1.4, 0.5 Hz), 8.25 (1H, m)

EIMS m/z (relative intensity): 392 (M$^+$, 100)

Elementary Analysis: for C$_{19}$H$_{18}$F$_2$N$_2$OS$_2$

Calculated: C 58.15; H 4.62; N 7.14

Measured: C 58.17; H 4.54; N 7.11

Example 56

Production of 10-(benzothiazol-2-ylthio)-N-(2,4-difluorophenyl)decanamide:

According to the same process as in Example 15, the intended product was obtained as colorless needle-like crystals.

m.p.: 91–92° C.

IR (KBr) cm$^{-1}$: 3439, 3299, 1668, 1528, 1429

$^1$H-NMR (CDCl$_3$) δ: 1.25–1.55 (10H, m), 1.64–1.87 (4H, m), 2.38 (2H, t, J=7.3 Hz), 3.34 (2H, t, J=7.3 Hz), 6.81–6.91 (2H, m), 7.20 (1H, br s), 7.29 (1H, ddd, J=8.0, 7.3, 1.5 Hz), 7.41 (1H, ddd, J=8.0, 7.3, 1.5 Hz), 7.75 (1H, ddd, J=8.0, 1.5, 1.2 Hz), 7.86 (1H, ddd, J=8.0, 1.5, 1.2 Hz), 8.26 (1H, m)

EIMS m/z (relative intensity): 448 (M$^+$, 100)

Elementary Analysis: for C$_{23}$H$_{26}$F$_2$N$_2$OS$_2$

Calculated: C 61.58; H 5.84; N 6.24

Measured: C 61.61; H 5.98; N 6.18

Example 57

Production of 5-(benzothiazol-2-ylthio)-N-(2,6-diisopropylphenyl)-2,2-dimethylpentanamide:

According to the same process as in Example 16, the intended product was obtained as colorless needle-like crystals.

m.p.: 129–131° C.

IR (KBr) cm$^{-1}$: 3319, 2963, 1640, 1510, 1426

$^1$H-NMR (d$_6$-DMSO) δ: 1.11 (12H, d, J=7.1 Hz), 1.29 (6H, s), 1.78–1.97 (4H, m), 3.07 (2H, sept, J=7.1 Hz), 3.40 (2H, t, J=6.8 Hz), 7.10 (1H, d, J=7.1 Hz), 7.11 (1H, d, J=7.1 Hz), 7.21 (1H, dd, J=8.3, 7.1 Hz), 7.35 (1H, td, J=7.3, 1.2 Hz), 7.45 (1H, td, J=7.3, 1.2 Hz), 7.84 (1H, ddd, J=7.3, 1.2, 0.7 Hz), 7.95 (1H, ddd, J=7.3, 1.2, 0.7 Hz), 8.42 (1H, br s)

EIMS m/z (relative intensity): 454 (M$^+$, 100)

Elementary Analysis: for C$_{26}$H$_{34}$N$_2$OS$_2$

Calculated: C 69.68; H 7.54; N 6.16; S 14.10

Measured: C 70.58; H 8.10; N 9.24; S 14.28

Example 58

Production of 6-(benzothiazol-2-ylthio)-N-(2-isopropyl-6-methylphenyl)hexanamide:

According to the same process as in Example 19, the intended product was obtained as colorless needle-like crystals.

m.p.: 77–78° C.

IR (KBr) cm$^{-1}$: 3235, 2960, 1637, 1530, 1430, 1001, 750

$^1$H-NMR (d$_6$-DMSO) δ: 1.08 (6H, d, J=6.8 Hz), 1.43 1.59 (2H, m), 1.60–1.75 (2H, m), 1.75–1.89 (2H, m), 2.09 (3H, s), 2.25–2.35 (2H, m), 3.08 (1H, sept, J=6.8 Hz), 3.34 (2H, t, J=7.3 Hz), 6.99 (1H, br s), 7.06 (2H, br s), 7.29 (1H, t, J=7.6 Hz), 7.40 (1H, t, J=7.6 Hz), 7.78 (1H, d, J=7.7 Hz), 7.89 (1H, d, J=7.7 Hz), 8.67 (1H, br s)

EIMS m/z (relative intensity): 412 (M$^+$)

Elementary Analysis: for C$_{23}$H$_{28}$N$_2$OS$_2$

Calculated: C 66.95; H 6.84; N 6.79

Measured: C 66.88; H 6.90; N 6.82

Example 59

Production of 6-(benzothiazol-2-ylthio)-N-(3,4,5-trimethoxyphenyl)hexanamide:

According to the same process as in Example 20, the intended product was obtained as colorless needle-like crystals.

m.p.: 92–93° C.

IR (KBr) cm$^{-1}$: 3432, 3304, 2933, 1652, 1512

$^1$H-NMR (CDCl$_3$) δ: 1.51–1.65 (2H, m), 1.80 (2H, quint, J=7.3 Hz), 1.89 (2H, quint, J=7.3 Hz), 2.37 (2H, t, J=7.3 Hz), 3.35 (2H, t, J=7.3 Hz), 3.81 (3H, s), 3.82 (6H, s), 6.84 (2H, s), 7.28 (2H, br s), 7.29 (1H, ddd, J=8.0, 7.3, 1.2 Hz), 7.42 (1H, ddd, J=8.0, 7.3, 1.2 Hz), 7.76 (1H, ddd, J=7.3, 1.2, 0.5 Hz), 7.86 (1H, ddd, J=7.3, 1.2, 0.5 Hz)

EIMS m/z (relative intensity): 446 (M$^+$, 100)

Elementary Analysis: for C$_{22}$H$_{26}$N$_2$O$_4$S$_2$

Calculated: C 59.17; H 5.87; N 6.27

Measured: C 58.96; H 5.89; N 6.23

Example 60

Production of N-[2-(benzoxazol-2-ylthio)ethyl]-N'-(2,6-diisopropylphenyl)urea:

Diphenylphosphoryl azide (DPPA) (133 mg, 0.48 mmols) was added to a DMF (1 ml) solution of 3-(benzoxazol-2-ylthio)propionic acid (98 mg, 0.44 mmols) and triethylamine (49 mg, 0.48 mmols), and stirred at room temperature for 4 hours. The reaction mixture was diluted with water, and extracted with ether. The organic layer was washed with water, and dried with anhydrous magnesium sulfate, and the solvent was evaporated. A chloroform (3 ml) solution of the thus obtained 3-(benzoxazol-2-ylthio)propionic acid azide (119 mg, 0.48 mmols) was heated under reflux for 30 minutes, to which was added a chloroform (1 ml) solution of 2,6-diisopropylaniline (85 mg, 0.48 mmols), and heated under reflux for further 15 hours. After the reaction, the solvent was evaporated, and the residue was purified through silica gel column chromatography (developer: hexane/ethyl acetate=3/1). The resulting crystals were recrystallized from ethyl acetate-hexane to obtain 54 mg (yield: 31%) of the intended product as colorless needle-like crystals.

m.p.: 197–198° C.

IR (KBr) cm$^{-1}$: 3384, 3317, 2963, 1659, 1536

$^1$H-NMR (d$_6$-DMSO) δ: 1.08 (12H, d, J=6.8 Hz), 3.08 (2H, sept, J=6.8 Hz), 3.54–3.61 (2H, m), 4.29 (2H, t, J=6.1 Hz), 5.98 (1H, br s), 7.04–7.19 (4H, m), 7.25–7.36 (2H, m), 7.42–7.48 (2H, m)

EIMS m/z (relative intensity): 397 (M$^+$) 247 (100)

Elementary Analysis: for C$_{22}$H$_{27}$N$_3$O$_2$S Calculated: C 66.47; H 6.85; N 10.57 Measured: C 66.38; H 6.95; N 10.45

Example 61

Production of N-[4-(benzoxazol-2-ylthio)butyl]-N'-(2,6-diisopropylphenyl)urea:

DPPA (181 mg, 0.66 mmols) was added to a DMF (1 ml) solution of 5-(benzoxazol-2-ylthio)pentanoic acid (150 mg, 0.60 mmols) and triethylamine (66 mg, 0.66 mmols), and stirred at room temperature for 4 hours. The reaction mixture was diluted with water, and extracted with ether. The organic layer was washed with water, and dried with anhydrous magnesium sulfate, and the solvent was evaporated. A chloroform (3 ml) solution of the thus obtained 5-(benzoxazol-2-ylthio)pentanoic acid azide (147 mg, 0.53 mmols) was heated under reflux for 30 minutes, to which was added a chloroform (1 ml) solution of 2,6-diisopropylaniline (106 mg, 0.60 mmols), and heated under reflux for further 17 hours. After the reaction, the solvent was evaporated, and the residue was purified through silica gel column chromatography (developer: hexane/ethyl acetate=3/1). The resulting crystals were recrystallized from ethyl acetate-hexane to obtain 99 mg (yield: 39%) of the intended product as colorless needle-like crystals.

m.p.: 179–180° C.

IR (KBr) cm$^{-1}$: 3334, 3262, 2966, 1626, 1134

$^1$H-NMR (d$_6$-DMSO) δ: 1.14 (12H, d, J=7.1 Hz), 1.57–1.69 (2H, m), 1.80–1.93 (2H, m), 3.11–3.21 (2H, m), 3.17 (2H, sept, J=7.1 Hz), 3.38 (2H, t, J=7.2 Hz), 5.70 (1H, br s), 7.02–7.23 (4H, m), 7.26–7.36 (2H, m) 7.55–7.63 (2H, m)

EIMS m/z (relative intensity): 425 (M$^+$), 203 (100)

Elementary Aanalysis: for C$_{24}$H$_{31}$N$_3$O$_2$S Calculated: C 67.73; H 7.34; N 9.87 Measured: C 67.61; H 7.35; N 9.85

Example 62

Production of N-[7-(benzoxazol-2-ylthio)heptyl]-N'-(2,6-diisopropylphenyl)urea:

DPPA (123 mg, 0.45 mmols) was added to a DMF (1 ml) solution of 8-bromooctanoic acid (100 mg, 0.45 mmols) and potassium carbonate (68 mg, 0.49 mmols), and stirred at room temperatures for 3 hours. The reaction mixture was diluted with water, and extracted with ether. The organic layer was washed with water, and dried with anhydrous magnesium sulfate, and the solvent was evaporated. A chloroform (2 ml) solution of the resulting 8-bromooctanoic acid azide (95 mg, 0.38 mmols) was heated under reflux for 30 minutes, to which was added a chloroform (1 ml) solution of 2,6-diisopropylaniline (68 mg, 0.38 mmols), and heated under reflux for further 15 hours. After the reaction, the solvent was evaporated, and the residue was purified through preparative thin-layer chromatography (developer: chloroform/methanol=20/1) to obtain 112 mg (yield: 63%) of N-(7-bromoheptyl)-N'-(2,6-diisopropylphenyl)urea as colorless powdery crystals.

Potassium carbonate (19 mg, 0.14 mmols) and 18-crown-6 (3 mg, 0.01 mmols) were added to DMF (3 ml) solution of the resulting bromine compound (50 mg, 0.13 mmols) and 2-mercaptobenzoxazole (19 mg, 0.14 mmols), and stirred at 80° C. for 2 hours. The reaction mixture was diluted with water, and extracted with ethyl acetate. The organic layer was washed with water, and dried with anhydrous magnesium sulfate, and the solvent was evaporated. The residue was purified through preparative thin-layer chromatography (developer: hexane/ethyl acetate=3/2), and the resulting crystals were recrystallized from ethyl acetate-hexane. 48 mg (yield: 82%) of the intended product was obtained as colorless needle-like crystals.

m.p.: 129–130° C.

IR (KBr) cm$^{-1}$: 3313, 2929, 1625, 1501, 1130

$^1$H-NMR (d$_6$-DMSO) δ: 1.15 (12H, d, J=6.8 Hz), 1.34–1.52 (8H, m), 1.78–1.89 (2H, m), 3.07–3.14 (2H, m), 3.21 (2H, sept, J=6.8 Hz), 3.35 (2H, t, J=7.1 Hz), 5.60 (1H, br s), 7.02–7.23 (4H, m), 7.29–7.35 (2H, m), 7.56–7.63 (2H, m)

EIMS m/z (relative intensity): 467 (M$^+$), 203 (100)

Elementary Analysis: for C$_{27}$H$_{37}$N$_3$O$_2$S Calculated: C 69.34; H 7.97; N 8.99 Measured: C 69.25; H 8.15; N 9.22

Example 63

Production of N-[2-(benzothiazol-2-ylthio)ethyl]-N'-(2,6-diisopropylphenyl)urea:

DPPA (63 mg, 0.23 mmols) was added to a DMF (0.5 ml) solution of 3-(benzothiazol-2-ylthio)propionic acid (50 mg, 0.21 mmols) and triethylamine (23 mg, 0.23 mmols), and stirred at room temperature for 3 hours. The reaction mixture was diluted with water, and extracted with ether. The organic layer was washed with water, and dried with anhydrous magnesium sulfate, and the solvent was evaporated. A chloroform (2 ml) solution of the thus obtained 3-(benzothiazol-2-ylthio)propionic acid azide (55 mg, 0.21 mmols) was heated under reflux for 30 minutes, to which was added a chloroform (1 ml) solution of 2,6-diisopropylaniline (39 mg, 0.22 mmols), and heated under reflux for further 13 hours. After the reaction, the solvent was evaporated, and the residue was purified through preparative thin-layer chromatography (developer: hexane/acetone=4/1). The resulting crystals were recrystallized from acetone-hexane-ether to obtain 32 mg (yield: 37%) of the intended product as colorless needle-like crystals.

m.p.: 197–198° C.

IR (KBr) cm$^{-1}$: 3385, 3304, 2962, 1648, 1375

$^1$H-NMR (d$_6$-DMSO) δ: 1.13 (12H, d, J=7.0 Hz), 3.13 (2H, sept, J=7.0 Hz), 3.51–3.58 (2H, m), 4.55 (2H, t, J=6.5 Hz), 6.05 (1H, br s), 7.08–7.23 (4H, m), 7.36 (1H, m), 7.47 (1H, m), 7.62–7.71 (2H, m)

EIMS m/z (relative intensity): 413 (M$^+$), 203 (100)

Elementary Analysis: for C$_{22}$H$_{27}$N$_3$OS$_2$ Calculated: C 63.89; H 6.58; N 10.16 Measured: C 63.59; H 6.70; N 10.00

Example 64

Production of N-[2-(benzoxazol-2-ylthio)ethyl]-N'-(2,4-difluorophenyl)urea:

DPPA (152 mg, 0.55 mmols) was added to a DMF (1 ml) solution of 3-(benzoxazol-2-ylthio)propionic acid (112 mg, 0.50 mmols) and triethylamine (56 mg, 0.55 mmols), and stirred at room temperature for 4 hours. The reaction mixture was diluted with water, and extracted with ether. The organic layer was washed with water, and dried with anhydrous magnesium sulfate, and the solvent was evaporated. A chloroform (3 ml) solution of the thus obtained 3-(benzoxazol-2-ylthio)propionic acid azide (123 mg, 0.50 mmols) was heated under reflux for 30 minutes, to which was added a chloroform (1 ml) solution of 2,4-difluoroaniline (65 mg, 0.50 mmols), and heated under reflux for further 15 hours. After the reaction, the solvent was evaporated, and the residue was purified through silica gel column chromatography (developer: hexane/ethyl acetate=3/1). The resulting crystals were recrystallized from ethyl acetate-hexane to obtain 94 mg (yield: 54%) of the intended product as colorless needle-like crystals.

m.p.: 228–229° C.

IR (KBr) cm$^{-1}$: 3311, 1649, 1435, 1396, 1282

$^1$H-NMR (d$_6$-DMSO) δ: 3.54–3.63 (2H, m), 4.32 (2H, t, J=6.1 Hz), 6.52 (1H, br s), 6.88 (1H, m), 7.03 (1H, m), 7.22–7.34 (2H, m) 7.38–7.48 (2H, m), 7.73–7.85 (2H, m)

EIMS m/z (relative intensity): 349 (M$^+$), 199 (100)

Elementary Analysis: for C$_{16}$H$_{13}$F$_2$N$_3$O$_2$S Calculated: C 55.01; H 3.75; N 12.03 Measured: C 55.28; H 3.80; N 12.04

Example 65

Production of N-[4-(benzoxazol-2-ylthio)butyl]-N'-(2,4-difluorophenyl)urea:

DPPA (181 mg, 0.66 mmols) was added to a DMF (1 ml) solution of 5-(benzoxazol-2-ylthio)pentanoic acid (150 mg, 0.60 mmols) and triethylamine (66 mg, 0.66 mmols), and stirred at room temperature for 4 hours. The reaction mixture was diluted with water, and extracted with ether. The organic layer was washed with water, and dried with anhydrous magnesium sulfate, and the solvent was evaporated. A chloroform (2 ml) solution of the thus obtained 5-(benzoxazol-2-ylthio)pentanoic acid azide (147 mg, 0.53 mmols) was heated under reflux for 30 minutes, to which was added a chloroform (1 ml) solution of 2,4-difluoroaniline (77 mg, 0.60 mmols), and heated under reflux for further 15 hours. After the reaction, the solvent was evaporated, and the residue was purified through silica gel column chromatography (developer: hexane/ethyl acetate=3/1). The resulting crystals were recrystallized from ethyl acetate-hexane to obtain 82 mg (yield: 36%) of the intended product as colorless needle-like crystals.

m.p.: 112–113° C.

IR (KBr) cm$^{-1}$: 3328, 2943, 1641, 1501, 1453

$^1$H-NMR (CDCl$_3$) δ: 1.67–1.79 (2H, m), 1.87–2.00 (2H, m), 3.29–3.42 (4H, m), 5.35 (1H, br s), 6.41 (1H, s), 6.76–6.88 (2H, m), 7.21–7.33 (2H, m), 7.45 (1H, m), 7.59 (1H, m), 7.97 (1H, m)

EIMS m/z (relative intensity): 377 (M$^+$), 155 (100)

Elementary Analysis: for C$_{18}$h$_{17}$f$_2$N$_3$O$_2$S Calculated: C 57.28; H 4.54; N 11.13 Measured: C 57.42; H 4.55; N 11.06

Example 66

Production of 9-(benzoxazol-2-ylsulfinyl)-N-(2,6-diisopropylphenyl)nonanamide:

m-Chloroperoxybenzoic acid (206 mg, 0.80 mmols) was added to a methylene chloride (2 ml) solution of 9-(benzoxazol-2-ylthio)-N-(2,6-diisopropylphenyl) nonanamide (187 mg, 0.40 mmols) cooling in ice bath, and stirred for 15 minutes. The reaction mixture was diluted with 10% solution of sodium hydrogensulfite, and extracted with ethyl acetate. The organic layer was washed with an aqueous saturated solution of sodium hydrogencarbonate, water, and saturated saline in that order, and dried with anhydrous sodium sulfate, and the solvent was evaporated. Then, the residue was purified through silica gel column chromatography (20 g of silica gel), developer: hexane:acetone= 5:1–10:3), and resulting crystals were recrystallized from hexane-acetone-pentane, and colorless crystals 54 mg (yield: 28%) of the intended product as crystals.

m.p.: 71–73° C.

IR (KBr) cm$^{-1}$: 3434, 3238, 2964, 1646, 1089

$^1$H-NMR (d$_6$-DMSO) δ: 1.12 (12H, d, J=6.8 Hz), 1.34–1.89 (12H, m), 2.32 (3H, s), 3.09 (2H, sept, J=6.8 Hz), 3.31–3.49 (2H, m), 7.09 (1H, d, J=8.4 Hz), 7.09 (1H, d, J=6.8 Hz), 7.19 (1H, dd, J=8.4, 6,8 Hz), 7.50 (2H, td, J=7.6, 1.4 Hz), 7.78 (2H, ddd, J=7.6, 1.4, 0.9 Hz), 8.61 (1H, br s)

EIMS m/z (relative intensity): 466 (M$^+$–16), 204 (100)

Elementary Analysis: for C$_{28}$H$_{38}$N$_2$O$_3$S Calculated: C69.68; H 7.93; N 5.80; S 6.64 Measured: C 69.52; H 7.86; N 5.79; S 6.69

Example 67

Production of 9-(benzoxazol-2-ylsulfonyl)-N-(2,6-diisopropylphenyl)nonanamide:

m-Chloroperoxybenzoic acid (322 mg, 1.25 mmols) was added to a methylene chloride (3 ml) solution of 9-(benzoxazol-2-ylthio)-N-(2,6-diisopropylphenyl) nonanamide 2 (233 mg, 0.50 mmols) cooling in ice bath, and stirred for 30 minutes, and then stirred for 1.5 hours at room temperature. The reaction mixture was diluted with 10% solution of sodium hydrogensulfite, and extracted with ethyl acetate. The organic layer was washed with an aqueous saturated solution of sodium hydrogencarbonate, water, and saturated saline in that order, and dried with anhydrous sodium sulfate, and the solvent was evaporated. Then, the residue was purified through silica gel column chromatography (15 g of silical gel, developer: hexane:acetone= 5:1–5:2), and the resulting crystals were recrystallized from acetone-hexane-ether, and colorless needle-like crystals 192 mg (yield: 77%) of the intended product as crystals.

m.p.: 108–111° C.

IR (KBr) cm$^{-1}$: 3431, 3230, 2931, 1647, 1346

$^1$H-NMR (d$_6$-DMSO) δ: 1.12 (12H, d, J=6.8 Hz), 1.26–1.69 (10H, m), 1.85 (2H, quint, J=7.6 Hz), 2.32 (2H, m), 3.09 (2H, sept, J=6.8 Hz), 3.66 (2H, t, J=7.6 Hz), 7.08 (1H, d, J=8.5 Hz), 7.09 (1H, d, J=6.6 Hz), 7.19 (1H, dd, J=8.5, 6.6 Hz), 7.54 (1H, ddd, J=8.1, 7.3, 1.5 Hz) 7.62 (1H, ddd, J=7.8, 7.3, 1.5 Hz) 7.83 (1H, ddd, J=8.1, 1.5, 0.8 Hz) 7.92 (1H, ddd, J=7.8, 1.5, 0.8 Hz), 8.59 (1H, br s)

Elementary Analysis: for C$_{28}$h$_{38}$N$_2$O$_4$S Calculated: C 67.44; H 7.68; N 5.62; S 6.64 Measured: C 67.38; H 7.70; N 5.61; S 6.69

Example 68

Production of 2-(benzoxazol-2-ylthio)-N-(2,4,6-trifluorophenyl)acetoamide:

Potassium carbonate (61 mg, 0.44 mmols) was added to an acetone (2 ml) solution of 2-mercaptobenzoxazole (60 mg, 0.4 mmols) and 2-bromo-N-(2,4,6-trifluorophenyl) acetoamide (107 mg, 0.4 mmols), and stirred for 40 minutes at room temperature. The reaction mixture was filtered, and then solvent was evaporated under reduced pressure therefrom, and the obtained residue was diluted with water, and extracted with chloroform. The organic layer was washed with water and saturated saline in that order, and dried with anhydrous magnesium sulfate, and the solvent was evaporated. Then, the residue was purified through preparative thin-layer chromatography (developer: methylene chlloride:hexane:ether=6:6:1), and the resulting crystals were recrystallized from acetone-hexane, and colorless needle-like crystals 79 mg (yield: 59%) of the intended product as crystals.

m.p.: 138–140° C.

IR (KBr) cm$^{-1}$: 3432, 3263, 1683, 1545, 1510

$^1$H-NMR (d$_6$-DMSO) δ: 4.06 (2H, s), 6.66–6.76 (2H, m), 7.28–7.37 (2H, m) 7.50 (1H, m), 7.62 (1H, m), 9.33 (1H, br s)

Elementary Analysis: for C$_{15}$H$_9$F$_3$N$_2$O$_2$S Calculated: C 53.26; H 2.68; N 8.28 Measured: C 53.38; H 2.59; N 8.13

Example 69:

Production of 6-(benzoxazol-2-ylthio)-N-(2,4,6-triflurophenyl)hexanamide:

6-Bromohexanoyl chloride (234 mg, 1.1 mmols) was gradualy added dropwise to a chloroform (3 ml) solution of 2,4,6-trifluoroaniline (147 mg, 1.0 mmol) and triethylamine (11 mg, 1.1 mmols) cooling in ice bath, and stirred for 1 hour at room temperature. The reaction mixture was concentrated, and extracted with ethyl acetate. The organic layer was washed with 1N-HCl, an aqueous saturated solution of sodium hydrogencarbonate, water, and saturated saline in that order, and dried with anhydrous sodium sulfate, and the solvent was evaporated. Then, the resulting solid was recrystallized from hexan-ether, and 6-bromo-N-(2,4,6-trifluorophenyl)hexan amide 283 mg(yield 87%) was obtained as colorless needle-like crystals. Potassium carbonate (45 mg, 0.33 mmols) and 18-crown-6 (8 mg, 0.03 mmols) were added to DMF (2 ml) solution of the resulting anilide (97 mg, 0.3 mmols) and 2-mercaprbenzoxzole (45 mg, 0.3 mmol), and stirred for 1.5 hours at 80° C. The mixture was diluted with water, and extracted with ethyl acetate. The organic layer was washed with water and saturated saline in that order, and dried with anhydrous sodium sulfate, and the solvent was evaporated. And the resulting crystals were recrystallized from hexane-ether, and colorless needle-like crystals 106 mg (yield: 90%) of the intended product as crystals.

m.p.: 124–125° C.

IR (KBr) cm$^{-1}$: 3439, 3260, 1677, 1530, 1455

$^1$H-NMR (d$_6$-DMSO) δ: 1.55–1.65 (2H, m), 1.83 (2H, quint, J=7.2 Hz), 1.91 (2H, quint, J=7.2 Hz), 2.46 (2H, t, J=7.2 Hz), 3.32 (2H, t, J=7.2 Hz), 6.69–6.76 (2H, m) 6.84 (1H, br s), 7.21–7.30 (2H, m), 7.43 (1H, m), 7.57 (1H, m)

Elementary Analysis: for C$_{19}$H$_{17}$F$_3$N$_2$O$_2$S Calculated: C 57.86; H 4.34; N 7.10 Measured: C 57.98; H 4.38; N 6.98

Example 70

Production of 9-(benzoxazol-2-ylthio)-N-(2,4,6-trifluorophenyl)nonanamide:

Oxallyl chloride (95 mg, 0.75 mmol) was added to a chloroform (1 ml) solution of 9-bromononanoic acid (119 mg, 0.5 mmols) and a drop of DMF and the resulting mixture was stirred for 40 minutes at room temperature. The reaction mixture and toluene were azeotroped, and then a chloroform (1 ml) solution of the condensed residue was dropped in to a chloroform (0.5 ml) solution of 2,4,6-trifluoroaniline (74 mg, 0.5 mmols) and triethylamine (76 mg, 0.75 mmols) cooling in ice bath, and stirred for 90 minutes at room temperature. The resulting mixture was concentrated, and the resulting residue was diluted with ethyl accetate. The organic layer was washed with 0.5N-HCl, an aqueous saturated solution of sodium hydrogencarbonate, water, and saturated saline in that order, and dried with anhydrous sodium sulfate, and the solvent was evaporated. Then, the residue was purified through silica gel chromatography (silica gel 20 g, developer; hexane:acetone=20:3). And the resulting crystals were recrystallized from acetone-hexane, and 9-bromo-N-(2,4,6-trifluorophenyl) nonanamide 137 mg (yield: 75%) as colorless needle-like crystals (m.p. 65–66° C.). Potassium carbonate (69 mg, 0.45 mmols) and 18-crown-6 (8 mg, 0.03 mmols) were added to a DMF (1 ml) solution of the resulting anilide (110 mg, 0.3 mmols) and 2-mercaptbenzoxzole (45 mg, 0.3 mmol), and stirred for 3 hours at 80° C. The mixture was diluted with water, and extracted with ethyl accetate. The organic layer was washed with water and saturated saline in that order, and dried with anhydrous sodium sulfate, and the solvent was evaporated. And the resulting residue was purified through silica gel chromatography (silica gel 10 g, developer; hexane:acetone=5:2). And the resulting crystals were recrystallized from acetone-hexane, and the intended product 94 mg (yield: 72%) as colorless needle-like crystals.

m.p.: 108–109° C.

IR (KBr) cm$^{-1}$: 3437, 3261, 2930, 1678, 1533

$^1$H-NMR (d$_6$-DMSO) δ: 1.32–1.52 (8H, m), 1.73 (2H, m), 1.83 (2H, quint, J=7.3 Hz), 2.39 (2H, m) 3.31 (2H, t, J=7.3 Hz), 6.68–6.78 (3H, m), 7.20–7.31 (2H, m), 7.43 (1H, m), 7.60 (1H, m)

Elementary Analysis: for C$_{22}$H$_{23}$F$_3$N$_2$O$_2$S Calculated: C 60.54; H 5.31; N 6.42 Measured: C 60.47; H 5.51; N 6.41

Example 71:

Production of N-[6-(benzoxazol-2-ylthio)hexyl]-N'-(2,6-diisopropylphenyl)-N-heptyl urea:

A mixture of n-heptylamine (1.21 g, 10.5 mmols) and 6-hexanolactone (1.14 g, 10 mmols) was stirred at 100° C. for 3 hours, and then crystallized from ether-hexane to obtain 1.77 g (yield 78%) of N-heptyl-6-hydroxyhexaneamide as colorless crystal.

Lithium aluminium hydride (189 mg, 5 mmols) was added to an anhydride THF solution (7 ml) of the above amide (454 mg, 2 mmols), and the resulting mixture was refluxed for 2 hours under argon atmosphere. The reaction mixture was diluted with ether (30 ml), and an aqueous saturated solution of ammonium chloride (0.4 ml) was added to the mixture, and stirred for 30 minutes at room temperature, and dried with anhydrous potassium carbonate. And the mixture solution was filtered through a pad of Cerite. The filtrate was concentrated to obtain the residue, which was crystallized from ether and hexane, and 6-heptylamino-1-hexanol 223 mg (yield 52%) was obtained as colorless crystals. This amine (213 mg, 1 mmol) was added to a chloroform solution (2 ml) of 2,6-diisopropylphenylisocyanate (207 mg, 1 mmol), and stirred for 2 hours at room temperature. The solvent was evaporated, and the obtained residue was purified through silica gel column chromatography (silica gel 15 g, developer: chloroform:mrthanol=98:2). The resulting crystals were recrystallized from acetone-hexane to obtain 370 mg of N'-(2,6-di isopropylphenyl)-N-heptyl-N-(6-hydroxyhexyl) urea (yield: 88%) as colorless crystals.

Methane sulfonyl chloride (69 mg, 0.6 mmols) was added dropwise to an anhydrous THF solution (5 ml) of the above alcohol (210 mg, 0.5 mmols), triethylamine (71 mg, 0.7 mmols) and 4-dimethylaminopyridine (6 mg, 0.05 mmols) in cooling ice bath, and stirred for 2 hours. The solvent was evaporated, and diluted with ethyl accetate. The organic layer was washed with water and saturated saline in that order, and dried with anhydrous sodium sulfate, and the solvent was evaporated. Then, the residue was purified through silica gel chromatography (silica gel 10 g, developer; hexane:acetone=10:1). And the resulting crystals were recrystallized from acetone-hexane, and 152 mg (yield: 70%) of the intended product as colorless needle-like crystals.

m.p.: 125–126° C.

IR (KBr) cm$^{-1}$: 3338, 2929, 1623, 1505, 1454

$^1$H-NMR (d$_6$-DMSO) δ: 0.86 (3H, t, J=7.1 Hz), 1.11 (12H, d, J=6.8 Hz), 1.22–1.675 (16H, m), 1.81 (2H, quint, J=7.2 Hz), 3.15 (2H, sept, J=6.8 Hz), 3.23–3.37 (6H, m), 7.05 (1H, d, J=6.6 Hz), 7.15 (1H, dd, J=8.1, 6.6 Hz) 7.22–7.34 (2H, m), 7.50–7.61 (2H, m)

Elementary Analysis: for C$_{33}$H$_{49}$N$_3$O$_2$S Calculated: C 71.83; H 8.95; N 7.61 Measured: C 71.80; H 9.11; N 7.54

Advantages of the Invention

The present invention provides compounds having excellent ACAT inhibiting activities.

The compounds of the present invention, as having excellent ACAT inhibiting activities, especially selective ACAT inhibiting activities, are useful as pharmaceutical compositions with few side effects, especially as medicines for arteriosclerosis.

What is claimed is:

1. A compound of a general formula (I);

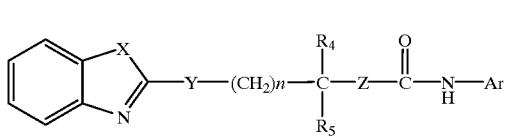

(1)

wherein Ar represents an optionally-substituted aryl group; $R_4$ and $R_5$ are the same or different, and each represents a hydrogen atom, a lower alkyl group having from 1 to 8 carbon atoms, or a lower alkoxy group having from 1 to 8 carbon atoms; $R_4$ and $R_5$ may together form a lower alkylene group having from 1 to 8 carbon atoms or lower alkylene group having from 1 to 8 carbon atoms of which are one or more methylene moieties is/are optionally substituted by oxygen and/or sulfur atoms;

X represents an oxygen atoms;

Y represents —NH—, a oxygen or sulfur atom or a sulfoxide or sulfone;

Z represents a single bond;

n represents an integer of from 0 to 15;

provided that, when Y is an oxygen atom, sulfur atom or a sulfoxide, then n must not be 0, when Y is a sulfur atom or sulfone, $R_4$ and $R_5$ are hydrogen atoms, then n must not be 0 or 2, and when Y is a sulfur atom or an oxygen atom, $R_4$ and $R_5$ are hydrogen atoms and n is 1, then Ar must not be a phenyl group;

or a salt or solvate thereof.

2. Anilide compounds of general formula (II):

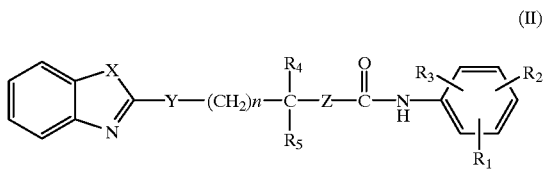

(II)

wherein $R_1$, $R_2$ and $R_3$ are the same or different, and each represents a hydrogen atom, a lower alkyl group having from 1 to 8 carbon atoms, a lower alkoxy group having from 1 to 8 carbon atoms, a halogen atom, a hydroxyl group, a phosphoric acid group, a sulfonamido group, or an optionally-substituted amino group; or any two of $R_1$, $R_2$ and $R_3$ together form an alkylenedioxy group having from 1 to 8 carbon atoms, or a lower alkoxy group having from 1 to 8 carbon atoms; $R_4$ and $R_5$ are the same or different, and each represents a hydrogen atom, a lower alkyl group having from 1 to 8 carbon atoms, or a lower alkoxy group having from 1 to 8 carbon atoms; or $R_4$ and $R_5$ may together form a lower alkylene group having from 1 to 8 carbon atoms, or a lower alkoxy group having from 1 to 8 carbon atoms, or a lower alikylene group having from 1 to 8 carbon atoms of which one or more methylene moieties is/are optionally substituted by oxygen and/or sulfur atoms;

X represents an oxygen atoms;

Y represents —NH—, a oxygen or sulfur atom or a sulfoxide or sulfone;

Z represents a single bond;

n represents an integer of from 0 to 15;

provided that, when Y is an oxygen atom, sulfur atom or a sulfoxide, then n must not be 0, when Y is a sulfur atom or sulfone, $R_4$ and $R_5$ are hydrogen atoms, then n must not be 0 or 2, and when Y is a sulfur atom or an oxygen atom, $R_4$ and $R_5$ are hydrogen atoms Z is a single bond and n is 1, then each $R_1$ to $R_3$ must not be hydrogen atoms, or a salt or solvate thereof.

3. A compound of claim 2 wherein Y is sulfur; Z is a single bond; n is 3 to 8 or 13; $R_1$ is 2-isopropyl; $R_2$ is hydrogen; $R_3$ is 6-isopropyl; and $R_4$ and $R_5$ are each hydrogen.

4. A compound of claim 2 wherein Y is sulfur; Z is a single bond; n is 3, 4 or 8; $R_1$ is 2-fluoro; $R_2$ is hydrogen; $R_3$ is 6-fluoro; and $R_4$ and $R_5$ are each hydrogen.

5. A compound of claim 2 wherein the compound is selected from the group consisting of 1) a compound wherein Y is sulfur; Z is a single bond; n is 3; $R_1$ is 2-isopropyl; $R_2$ is hydrogen; $R_3$ is 6-isopropyl; $R_4$ and $R_5$ are each hydrogen;

2) a compound wherein Y is sulfur; Z is a single bond; n is 4; $R_1$ is 2-propyl; $R_3$ is 6-propyl; $R_2$ is hydrogen; and $R_4$ and $R_5$ together are —(CH$_2$)$_4$—;

3) a compound wherein Y is sulfur; Z is a single bond; n is 4; $R_1$ is 2-isopropyl; $R_3$ is 6-isopropyl; and $R_4$ and $R_5$ together are —(CH$_2$)$_3$—;

4) a compound wherein Y is sulfur; Z is a single bond; n is 4; $R_1$ is 2-isopropyl; $R_3$ is 6-methyl; and $R_2$, $R_4$ and $R_5$ are each hydrogen; and 5) a compound wherein Y is sulfur; Z is a single bond; n is 7; $R_1$ is 2-isopropyl; $R_3$ is 6-isopropyl; and $R_1$, $R_4$ and $R_5$ are each hydrogen; a compound wherein Y is sulfur; Z is a single bond; n is 4; $R_1$ is 2-isopropyl; $R_3$ is 6-isopropyl; and $R_2$, $R_4$ and $R_5$ are each hydrogen.

6. A compound of claim 2 wherein Y is sulfur, n is 3 to 8 or 13; $R_1$ is 2-fluoro; $R_2$ is 2-fluoro; $R_3$ is 6-fluoro; and $R_4$ and $R_5$ are each hydrogen.

7. A compound of claim 2 wherein Y is sulfur; n is 3, 4 or 8; $R_1$ is 2-fluoro; $R_2$ is hydrogen; $R_3$ is 6-fluoro; and $R_4$ and $R_5$ are each hydrogen.

8. A compound of claim 2 wherein the compound is selected from the group consisting of 1) a compound wherein Y is sulfur; n is 3; $R_1$ is 2-isopropyl; $R_2$ is hydrogen; $R_3$ is 6-isopropyl; $R_4$ and $R_5$ are each hydrogen;

2) a compound wherein Y is sulfur; n is 4; $R_1$ is 2-propyl; $R_2$ is hydrogen; $R_3$ is 6-propyl; and $R_4$ and $R_5$ together are —(CH$_2$)$_4$—;

3) a compound wherein Y is sulfur; n is 4; $R_1$ is 2-isopropyl; $R_3$ is 6-isopropyl; and $R_4$ and $R_5$ together are —(CH$_2$)$_3$—;

4) a compound wherein Y is sulfur; n is 4; $R_1$ is 2-isopropyl; $R_3$ is 6-methyl; and $R_2$, $R_4$ and $R_5$ are each hydrogen; and 5) a compound wherein Y is sulfur, sulfoxide or sulfone; n is 7; $R_1$ is 2-isopropyl; $R_3$ is 6-isopropyl; and $R_2$, $R_4$ and $R_5$ are each hydrogen; and 6) a compound wherein Y is sulfur; Z is a single bond; n is 4; $R_1$ is 2-isopropyl; $R_3$ is 6-isopropyl; and $R_2$, $R_4$ and $R_5$ are each hydrogen.

9. A pharmaceutical composition comprising an effective amount of a compound of claim 1 or 2, or a salt or solvate thereof, and a pharmaceutically acceptable carrier.

10. A method for treating a mammal suffering from or susceptible to a disorder that can be treated with an ACAT inhibitor, an intracellular cholesterol transference inhibitor, a blood cholesterol depressant, or an anti-foaming agent for macrophages, which comprises administering to the mammal an effective dosage of a compound of a general formula (III):

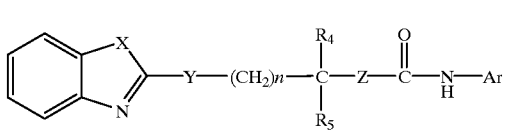

wherein Ar represents an optionally substituted aryl group; $R_4$ and $R_5$ are the same or different, and each represents a hydrogen atom, a lower alkyl group having from 1 to 8 carbon atoms, or a lower alkoxy group having from 1 to 8 carbon atoms;

or $R_4$ and $R_5$ may together form a lower alkylene group having from 1 to 8 carbon atoms of which are one or more methylene moieties is/are optionally substituted by oxygen and/or sulfur atoms;

X represents an oxygen atom;

Y represents —NH—, an oxygen atom or a sulfur atom, or a sulfoxide or sulfone;

Z represents a single bond; and n represents an integer of from 0 to 15;

or salt or solvate thereof.

11. A method of claim 10, wherein the mammal is suffering from or susceptible to hyperlipemia, arteriosclerosis, cerebrovascular disorders, ischemic cardiopathy, ischemic enteropathy or aortic aneurysm.

12. A method of claim 11 wherein Y is sulfur; n is 3 to 8 or 13; $R_1$ is 2-isopropyl; $R_2$ is hydrogen; $R_3$ is 6-isopropyl; and $R_4$ and $R_5$ are each hydrogen.

13. A method of claim 11 wherein Y is sulfur; n is 3, 4, or 8; $R_1$ is 2-fluoro; $R_2$ is hydrogen; $R_3$ is 6-fluoro; and $R_4$ and $R_5$ are each hydrogen.

14. A method of claim 11 wherein the compound is selected from the group consisting of 1) a compound wherein Y is sulfur; n is 3; $R_1$ is 2-isopropyl; $R_3$ is 6-isopropyl; and $R_2$, $R_4$ and $R_5$ are each hydrogen;

2) a compound wherein Y is sulfur; n is 4; $R_1$ is 2-isopropyl; $R_2$ is hydrogen; $R_3$ is 6-propyl; and $R_4$ and $R_5$ together are —$(CH_2)_4$—;

3) a compound wherein Y is sulfur; n is 4; $R_1$ is 2-isopropyl; $R_2$ is hydrogen; $R_3$ is 6-propyl; and $R_4$ and $R_5$ together are —$(CH_2)_3$—;

4) a compound wherein Y is sulfur; n is 4; $R_1$ is 2-isopropyl; $R_3$ is 6-methyl; and $R_2$, $R_4$ and $R_5$ are each hydrogen;

5) a compound wherein Y is sulfur; n is 7; $R_1$ is 2-isopropyl; $R_3$ is 6-isopropyl; and $R_2$, $R_4$ and $R_5$ are each hydrogen; and 6) a compound wherein Y is sulfur; n is 4; $R_1$ is 2-isopropyl; $R_3$ is 6-isopropyl; and $R_2$, $R_4$ and $R_5$ are each hydrogen.

15. A method for treating a mammal suffering from or susceptible to a disorder that can be treated with an ACAT inhibitor, an intracellular cholesterol transference inhibitor, a blood cholesterol depressant, or an anti-foaming agent for macrophages, which comprises administering to the mammal an effective dosage of a compound of a general formula (IV):

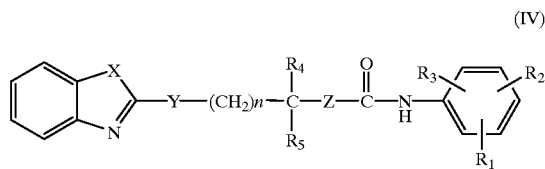

wherein $R_1$, $R_2$ and $R_3$ are the same or different, and each represents a hydrogen atom, a lower alkyl group having from 1 to 8 carbon atoms, a lower alkoxy group having from 1 to 8 carbon atoms, a halogen, a hydroxyl group, a phosphoric acid group, a sulfonamido group, or an optionally-substituted amino group; or any two of $R_1$, $R_2$ and $R_3$ together form an alkylenediosy group having from 1 to 8 carbon atoms; $R_4$ and $R_5$ are the same or different, and each represents a hydrogen atom, a lower alkyl group having from 1 to 8 carbon atoms, or a lower alkoxy group having from 1 to 8 carbon atoms; or $R_4$ and $R_5$ may together form a lower form a lower alkylene group having from 1 to 8 carbon atoms of which one or methylene moieties is/are optionally substituted by oxygen and/or sulfur atoms;

X represents an oxygen atom;

Y represents —NH—, an oxygen or a sulfur atom, or a sulfoxide or sulfone;

Z represents a single bond;

n represents an integer of from 0 to 15;

or a salt or solvate thereof.

16. A method of claim 15 wherein the mammal is suffering from or susceptible to hyperlipemia, arteriosclerosis, cerebrovascular disorders, ischemic cardiopathy, ischemic enteropathy or aortic aneurysm.

17. A method of claim 16 wherein Y is sulfur; Z is a single bond; n is 3 to 8 or 13; $R_1$ is 2-isopropyl; $R_2$ is hydrogen; $R_3$ is 6-isopropyl; and $R_4$ and $R_5$ are each hydrogen.

18. A method of claim 16 wherein Y is sulfur; Z is a single bond; n is 3, 4, or 8; $R_1$ is 2-fluoro; $R_2$ is hydrogen; $R_3$ is 6-fluoro; and $R_4$ and $R_5$ are each hydrogen.

19. A method of claim 16 wherein the compound is selected from the group consisting of:

1) a compound wherein Y is sulfur; Z is a single bond; n is 3; $R_1$ is 2-isopropyl; $R_3$ is 6-isopropyl; and $R_2$, $R_4$ and $R_5$ are each hydrogen;

2) a compound wherein Y is sulfur; Z is a single bond; n is 4; $R_1$ is 2-isopropyl; $R_2$ is hydrogen; $R_3$ is 6-propyl; and $R_4$ and $R_5$ together are —$(CH_2)_4$—;

3) a compound wherein Y is sulfur; Z is a single bond; n is 4, $R_1$ is 2-isopropyl; $R_2$ is hydrogen; $R_3$ is 6-propyl; and $R_4$ and $R_5$ together are —$(CH_2)_3$—;

4) a compound wherein Y is sulfur; Z is a single bond; n is 4; $R_1$ is 2-isopropyl; $R_3$ is 6-methyl; and $R_2$, $R_4$ and $R_5$ are each hydrogen;

5) a compound wherein Y is sulfur; Z is a single bond; n is 7; $R_1$ is 2-isopropyl; $R_3$ is 6-isopropyl; and $R_2$, $R_4$ and $R_5$ are each hydrogen; and 6) a compound wherein Y is sulfur; Z is a single bond; n is 4; $R_1$ is 2-isopropyl; $R_3$ is 6-isopropyl; and $R_2$, $R_4$ and $R_5$ are each hydrogen.

* * * * *